US009187402B2

(12) United States Patent
Sang

(10) Patent No.: US 9,187,402 B2
(45) Date of Patent: Nov. 17, 2015

(54) ASPIRIN DERIVATIVES AND USES THEREOF

(71) Applicant: Shengmin Sang, Concord, NC (US)

(72) Inventor: Shengmin Sang, Concord, NC (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 0 days.

(21) Appl. No.: 13/918,394

(22) Filed: Jun. 14, 2013

(65) Prior Publication Data

US 2013/0338120 A1 Dec. 19, 2013

Related U.S. Application Data

(60) Provisional application No. 61/791,826, filed on Mar. 15, 2013, provisional application No. 61/659,647, filed on Jun. 14, 2012.

(51) Int. Cl.

| | |
|---|---|
| ***A01N 37/36*** | (2006.01) |
| ***A61K 31/60*** | (2006.01) |
| ***C07C 69/78*** | (2006.01) |
| ***C07C 49/86*** | (2006.01) |
| ***C07C 69/86*** | (2006.01) |
| ***C07C 49/835*** | (2006.01) |

(52) U.S. Cl.

CPC ............... *C07C 69/78* (2013.01); *C07C 49/835* (2013.01); *C07C 49/86* (2013.01); *C07C 69/86* (2013.01)

(58) Field of Classification Search

None

See application file for complete search history.

(56) References Cited

U.S. PATENT DOCUMENTS

| | | | |
|---|---|---|---|
| 6,008,260 | A | 12/1999 | Pezzuto et al. |
| 2009/0215881 | A1 | 8/2009 | Delaire et al. |
| 2010/0120727 | A1 | 5/2010 | Xu |
| 2010/0255088 | A1 | 10/2010 | Ovil |

FOREIGN PATENT DOCUMENTS

WO WO 04000302 A1 * 12/2003

OTHER PUBLICATIONS

Athar et al., "Resveratrol: A review of preclinical studies for human cancer prevention", *Toxicology and Applied Pharmacology*, 2007, 224: 274-283.

Barnes et al., "Chemoprevention of Spontaneous Intestinal Adenomas in the Adenomatous Polyposis Coli *Min* Mouse Model With Aspirin", *Gastroenterology*, 1998, 114: 873-877.

Baron et al., "A Randomized Trial of Aspirin to Prevent Colorectal Adenomas", *The New England Journal of Medicine*, 2003, 348(10): 891-899.

Barry et al., "Cyclooxygenase-2 Polymorphisms, Aspirin Treatment, and Risk for Colorectal Adenoma Recurrence—Data from a Randomized Clinical Trial", *Cancer Epidemiology, Biomarkers & Prevention*, 2009, 18: 2726-2733.

Berge et al. "Pharmaceutical Salts", *Journal of Pharmaceutical Science*, 1977, 66:1-19.

Chan et al., "Aspirin Use and Survival After Diagnosis of Colorectal Cancer", *Journal of the American Medical Association*, 2009, 302(6): 649-659.

Cui et al., "Resveratrol Suppresses Colitis and Colon Cancer Associated with Colitis", *Cancer Prevention Research*, 2010, 3(4): 549-560.

Cuzick et al,, "Aspirin and non-steroidal anti-inflammatory drugs for cancer prevention: an international consensus statement", *The Lancelot Oncology*, 2009, 10: 501-507.

Fiorucci et al., "Cyclooxygenase-2-Derived Lipoxin $A_4$ Increases Gastric Resistance to Aspirin-Induced Damage", *Gastroenterology*, 2002, 123(5): 1598-1606.

Gonzalez et al., "Effects of Flavonoids and other Polyphenols on Inflammation", *Critical Reviews in Food Science and Nutrition*, 2011, 51: 331-362.

Ho et al., "Antagonistic Effects of Aspirin and Folic Acid on Inflammation Markers and Subsequent Risk of Recurrent Colorectal Adenomas", *Journal of the National Cancer Institute*, 2009, 101(23): 1-5.

Hope et al., "Low concentrations of resveratrol inhibit Wnt signal throughput in colon-derived cells: Implications for colon cancer prevention", *Molecular Nutrition & Food Research*, 2008, 52: S52-S53.

Jacobs et al., "A Large Cohort Study of Long-Term Daily Use of Adult-Strength Aspirin and Cancer Incidence", *Journal of the National Cancer Institute*, 2007, 99(8): 608-615.

Lain E, Loren, "The Gastrointestinal Effects of Nonselective NSAIDs and COX-2-Selective Inhibitors", *Seminars in Arthritis and Rheumatism*, 2002, 32(3): 25-32.

Liu et al., "Effects of Combination of Calcium and Aspirin on Azoxymethane-Induced Aberrant Crypt Foci Formation in the Colons of Mice and Rats", *Nutrition and Cancer*, 2008, 60(5): 660-665.

Mashita et al., "Oral but Not Parenteral Aspirin Upregulates COX-2 Expression in Rat Stomachs", *Digestion*, 2006, 73: 124-132.

Miliaras et al., "The effect of aspirin and high fibre diet on colorectal carcinoma: a comparative experimental study", *Techniques in Coloproctology*, 2004, 8: S59-S61.

Nath et al., "Nitric oxide-donating aspirin inhibits β-catenin/T cell factor (TCF) signaling in SW480 colon cancer cells by disrupting the nuclear β-catenin/TFC association", *Proceedings of the National Academy of Sciences*, 2003, 100(22): 12584-12589.

Neugut, Alfred, "Aspirin as Adjuvant Therapy for Colorectal Cancer", *Journal of the American Medical Association*, 2009, 302(6): 688-689.

(Continued)

*Primary Examiner* — Craig Ricci

*Assistant Examiner* — Jared D Barsky

(74) *Attorney, Agent, or Firm* — Myers Bigel Sibley & Sajovec, P.A.

(57) ABSTRACT

The present invention provides novel aspirin derivatives useful for preventing and/or treating cancer. The novel compounds of this invention may be particularly useful for the prevention and/or treatment of cancers affecting the gastrointestinal system, such as colorectal cancer.

18 Claims, 5 Drawing Sheets

(56) References Cited

OTHER PUBLICATIONS

Pan et al., "Identification of molecular pathways affected by pterostilbene, a natural dimethylether analog of resveratrol", *BMC Medical Genomics*, 2008, 1:7.
Pan et al., "Pterostilbene Induces Apoptosis and Cell Cycle Arrest in Human Gastric Carcinoma Cells", *Journal of Agricultural and Food Chemistry*, 2007, 55: 7777-7785.
Pan et al., "Pterostilbene Suppressed Lipopolysaccharide-Induced Up-Expression of iNOS and COX-2 in Murine Macrophages", *Journal of Agricultural and Food Chemistry*, 2008, 56: 7502-7509.
Pan et al., "Pterostilbene inhibited tumor invasion via suppressing multiple signal transduction pathways in human hepatocellular carcinoma cells", *Carcinogenesis*, 2009, 30(7): 1234-1242.
Pan et al., "Suppression of Heregulin-β1/HER2-Modulated Invasive and Aggressive Phenotype of Breast Carcinoma by Pterostilbene via Inhibition of Matrix Metalloproteinase-9, p38 Kinase Cascade and Akt Activation", *Evidence-Based Complementary and Alternative Medicine*, 2011: pp. 1-12.
Paul et al,, "Anti-inflammatory Action of Pterostilbene Is Mediated through the p38 Mitogen-Activated Protein Kinase Pathway in Colon Cancer Cells", *Cancer Prevention Research*, 2009, 2(7): 650-657.
Paul et al., "Dietary intake of pterostilbene, a constituent of blueberries, inhibits the βcatenin/p65 downstream signaling pathway and colon carcinogenesis in rats", *Carcinogenesis*, 2010, 31(7): 1272-1278.
Rao et al., "Nitric oxide-releasing aspirin and indomethacin are potent inhibitors against colon cancer in azoxymethane-treated rats: effects on molecular targets", *Molecular Cancer Therapeutics*, 2006, 5(6): 1530-1538.
Reddy et al., "Inhibitory effect of aspirin on azoxymethane-induced colon carcinogenesis in F344 rats", *Carcinogenesis*, 1993, 14(8): 1493-1497.
Rigas et al., "NO-donating NSAIDs and cancer: An overview with a note on whether NO is required for their action", *Nitric Oxide*, 2008, 19: 199-204.
Rimando et al., "Cancer Chemopreventive and Antioxidant Activities of Pterostilbene, a Naturally Occurring Analogue of Resveratrol", *Journal of Agricultural and Food Chemistry*, 2002, 50: 3453-3457.
Sandler et al., "A Randomized Trial of Aspirin to Prevent Colorectal Adenomas in Patients with Previous Colorectal Cancer", *The New England Journal of Medicine*, 2003, 348(10): 883-890.
Schneider et al., "Resveratrol Inhibits Intestinal Tumorigenesis and Modulates Host-Defense-Related Gene Expression in an Animal Model of Human Familial Adenomatous Polyposis", *Nutrition and Cancer*, 2001, 39(1): 102-107.
Schneider et al., "Pterostilbene Inhibits Lung Cancer Through Induction of Apoptosis", *Journal of Surgical Research*, 2010, 161(1): 18-22.
Sengottuvelan et al., "Dietary supplementation of resveratrol suppresses colonic tumour incidence in 1,2-dimethylhydrazine-treated rats by modulating biotransforming enzymes and aberrant crypt foci development", *British Journal of Nutrition*, 2006, 96: 145-153.
Shao et al., "Structural identification of mouse urinary metabolites of pterostilbene using liquid chromatography/tandem mass spectrometry", *Rapid Communications in Mass Spectrometry*, 2010, 24: 1770-1778.
Solomon et al., "Cardiovascular Risk Associated with Celecoxib in a Clinical Trial for Colorectal Adenoma Prevention", *The New England Journal of Medicine*, 2005, 352(11): 1071-1080.
Stark et al., "Aspirin activates the NF-κB signalling pathway and induces apoptosis in intestinal neoplasia in two in vivo models of human colorectal cancer", *Carcinogenesis*, 2007, 28(5): 968-976.
Suh et al., "Pterostilbene, an Active Constituent of Blueberries, Suppresses Aberrant Crypt Foci Formation in the Azoxymethane-Induced Colon Carcinogenesis Model in Rats" *Clinical Cancer Research*, 2007, 13(1): 350-355.
Szekeres et al., "Chemopreventive effects of resveratrol and resveratrol derivatives", *Annals of the New York Academy of Sciences*, 2011, 1215: 89-95.
Tessitore et al., "Resveratrol depresses the growth of colorectal aberrant crypt foci by affecting *bax* and *p21*$^{CIP}$ expression", *Carcinogenesis*, 2000, 21(8): 1619-1622.
Wallace, John, "Nitric Oxide, Aspirin-Triggered Lipoxins and NO-Aspirin in Gastric Protection", *Inflammation & Allergy-Drug Targets*, 2006, 5(2): 133-137.
Xia et al., "Biological Activities of Polyphenols from Grapes", *International Journal of Molecular Sciences*, 2010, 11: 622-646.
Youn et al., "Resveratrol and Piceatannol Inhibit iNOS Expression and NF-κB Activation in Dextran Sulfate Sodium-Induced Mouse Colitis", *Nutrition and Cancer*, 2009, 61(6): 847-854.

* cited by examiner

ASPIRIN DERIVATIVES AND USES THEREOF

RELATED APPLICATIONS

This application claims priority under 35 U.S.C. §119(e) to U.S. Provisional Patent Application Ser. Nos. 61/791,826, filed Mar. 15, 2013, and 61/659,647, filed Jun. 14, 2012, the disclosure of each of which is incorporated herein by reference in its entirety.

STATEMENT OF FEDERAL SUPPORT

This invention was made with government support under 1-R03-CA159353-01A1, awarded by the National Institutes of Health. The government has certain rights in the invention.

FIELD OF THE INVENTION

The present invention generally relates to novel aspirin derivatives and the prevention and/or treatment of disorders responsive to aspirin derivatives.

BACKGROUND

Colorectal cancer (CRC) is a significant global health concern and is the third leading cause of death from cancer among both men and women worldwide.

Observational studies and randomized trials have demonstrated an inverse association between the incidence of CRC and the use of aspirin (acetylsalicylic acid), and aspirin has been shown to inhibit CRC tumorigenesis in various animal studies.

Because chronic aspirin administration gives rise to a number of adverse effects, including, but not limited to, gastrointestinal (GI) disturbances such as dyspepsia, gastroduodenal bleeding, gastric ulceration and gastritis, its usefulness in the prevention and/or treatment of CRC is limited.

There is thus a need for improved aspirin therapies to prevent and treat CRC.

SUMMARY OF THE INVENTION

The present invention provides aspirin derivatives and methods of making and using the same.

A first aspect of the present invention is a composition comprising, consisting essentially of or consisting of a compound of Formula I, II, III, IV, V, VI or VII.

A second aspect of the present invention is a pharmaceutical composition comprising, consisting essentially of or consisting of a compound of Formula I, II, III, IV, V, VI or VII and a pharmaceutically acceptable carrier.

A third aspect of the present invention is a method of producing a compound of Formula I, II, III, IV, V, VI or VII. In some embodiments, the method comprises, consists essentially of or consists of conjugating a first moiety and a second moiety, wherein the first moiety is aspirin, an aspirin analog or an aspirin derivative and the second moiety is stilbene (1,2-diphenylethene), an analog or derivative of stilbene, gingerol (6-gingerol; 5-hydroxy-1-(4-hydroxy-3-methoxyphenyl)-3-decanone), an analog derivative of ginergol, shogaol (6-shogaol; 1-(4-Hydroxy-3-methoxyphenyl)dec-4-en-3-one), an analog or derivative of shogaol, zingerone (4-(4-hydroxy-3-methoxyphenyl)-2-butanone) or an analog or derivative of zingerone.

A fourth aspect of the present invention is a method of preventing and/or treating a disorder in a subject in need thereof, comprising, consisting essentially of or consisting of administering to said subject a therapeutically effective amount of a composition comprising, consisting essentially of or consisting of a compound of Formula I, II, III, IV, V, VI or VII.

A fifth aspect of the present invention is a method of preventing and/or treating a disorder in a subject in need thereof, comprising, consisting essentially of or consisting of administering to said subject a pharmaceutical composition comprising, consisting essentially of or consisting of a compound of Formula I, II, III, IV, V, VI or VII and a pharmaceutically acceptable carrier.

A sixth aspect of the present invention is a kit for preventing and/or treating a disorder in a subject comprising, consisting essentially of or consisting of a compound or pharmaceutical composition of the present invention and instructions for using the compound or pharmaceutical composition.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
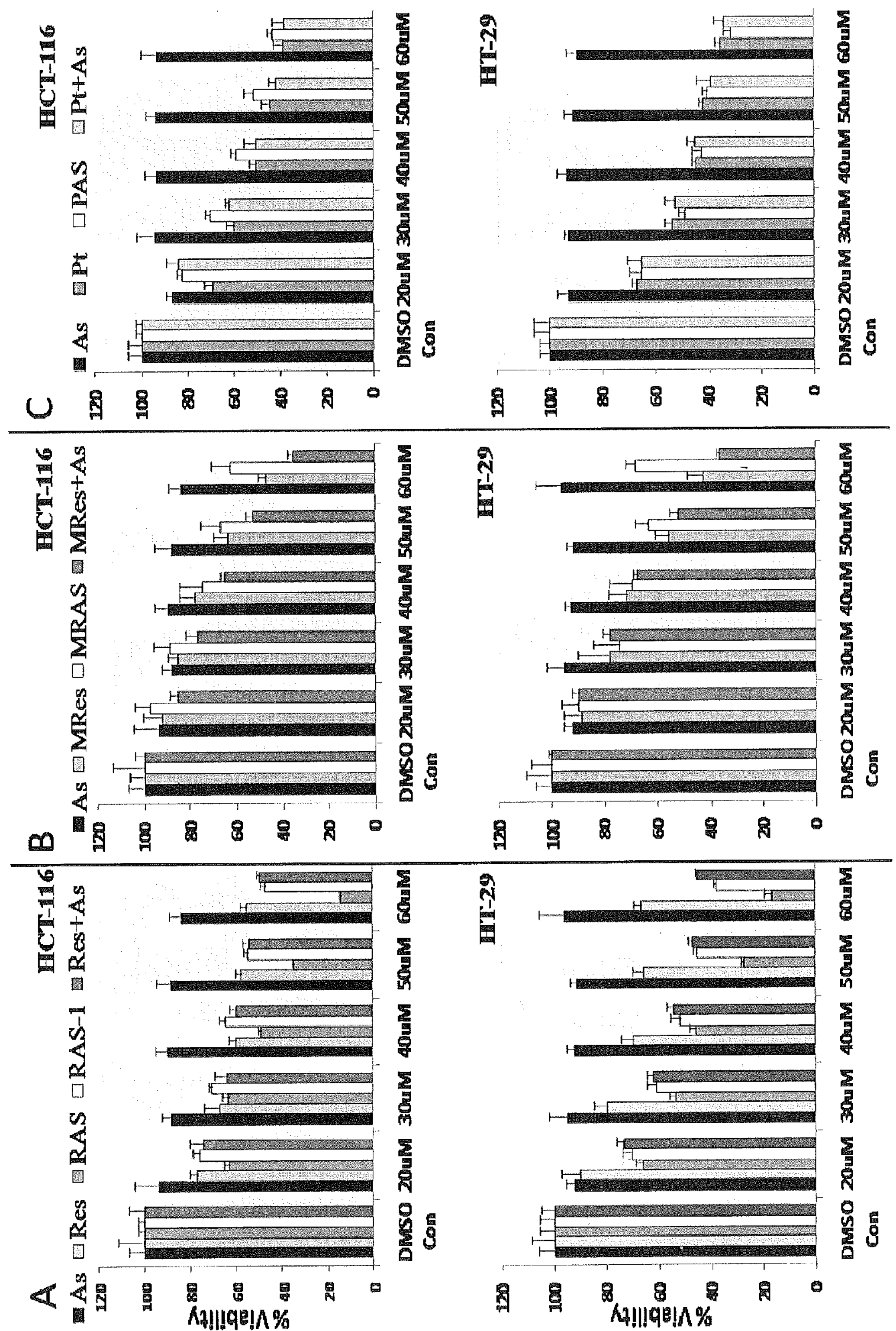
FIG. 1A shows the effects of aspirin (As), resveratrol (Res), 4'-aspirinated resveratrol (RAS), 1-aspirinated resveratrol (RAS-1), and the combination of resveratrol and aspirin (Res+As) on the growth of HCT-116 and HT-29 human colon cancer cells.
FIG. 1B shows the effects of aspirin (As), methylated-resveratrol (MRes), methylated-resveratrol aspirinate (MRAS) and the combination of MRes and aspirin (MRes+As) on the growth of HCT-116 and HT-29 human colon cancer cells.
FIG. 1C shows the effects of aspirin (As), pterostilbene (Pt), pterostilbene-aspirinate (PAS), and the combination of pterostilbene and aspirin (Pt+As) on the growth of HCT-116 and HT-29 human colon cancer cells.

The foregoing and other aspects of the present invention will now be described in more detail with respect to compositions and methodologies provided herein.

This description is not intended to be a detailed catalogue of all the ways in which the present invention may be implemented or of all the features that may be added to the present invention. For example, features illustrated with respect to one embodiment may be incorporated into other embodiments, and features illustrated with respect to a particular embodiment may be deleted from that embodiment. Thus, one or more of the method steps included in a particular method described herein may, in other embodiments, be omitted and/or performed independently. In addition, numerous variations and additions to the embodiments suggested herein, which do not depart from the instant invention, will be apparent to those skilled in the art in light of the instant disclosure. Hence, the following description is intended to illustrate some particular embodiments of the invention, and not to exhaustively specify all permutations, combinations and variations thereof. It should therefore be appreciated that the present invention is not limited to the particular embodiments set forth herein. Rather, these particular embodiments are provided so that this disclosure will convey the full scope of the invention to those skilled in the art.

The terminology used herein is for the purpose of describing particular embodiments of the present invention only and is not intended to limit the present invention.

Although the following terms are believed to be well understood by one of skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" pharmaceutically acceptable excipient can mean one pharmaceutically acceptable excipient or a plurality of pharmaceutically acceptable excipients.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "and/or" refers to and encompasses any and all possible combinations of one or more of the associated listed items, as well as the lack of combinations when interpreted in the alternative ("or").

As used herein, the term "cancer" refers to any benign or malignant abnormal growth of cells. Examples include, without limitation, breast cancer, prostate cancer, lymphoma, skin cancer, pancreatic cancer, colon cancer, colorectal cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers. In some embodiments, the cancer is colorectal cancer or lung cancer.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method of the present invention, refers to an increase or decrease in the effectiveness of the composition/method of at least about 20% or more. For example, a component added to a composition of the present invention would "materially alter" the composition if it increases or decreases the composition's ability to inhibit tumor growth by at least 20%.

As used herein, the term "derivative" refers to a compound that is structurally related to and can be derived from a second compound. Thus, an aspirin derivative is a compound that is structurally related to and can be derived from aspirin.

As used herein, the term "emulsion" refers to a suspension or dispersion of one liquid within a second immiscible liquid. In some embodiments, the emulsion is an oil-in-water emulsion or a water-in-oil emulsion. In some embodiments, "emulsion" may refer to a material that is a solid or semi-solid at room temperature and is a liquid at body temperature (about 37° C.).

As used herein, the terms "increase" and "enhance" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "reduce" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the term "optionally substituted" refers to a chemical structure that may comprise one or more substituents. Optionally substituted structures may comprise any suitable substituent, including, but not limited to, F, Cl, Br, I, $NH_2$, $NHCH_3$, $N(CH_3)_2$, SH, $SCH_3$, OH, O—$C_{1-6}$ alkyl, $C_{1-6}$ alkyl, and $C_{1-6}$ alkoxy.

As used herein, "pharmaceutically acceptable" means that the material is suitable for administration to a subject and will allow desired treatment to be carried out without giving rise to unduly deleterious adverse effects. The severity of the disease and the necessity of the treatment are generally taken into account when determining whether any particular side effect is unduly deleterious.

As used herein, the terms "prevent," "preventing," and "prevention" (and grammatical variants thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the compositions and/or methods of the present invention. In some embodiments, prevention is complete, resulting in the total absence of the disease, disorder and/or clinical symptom(s). In some embodiments, prevention is partial, resulting in reduced severity and/or delayed onset of the disease, disorder and/or clinical symptom(s).

As used herein, the term “prevention effective amount” (and grammatical variants thereof) refers an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, the term “subject” (and grammatical variants thereof) refers to mammals, avians, reptiles, amphibians, or fish. Mammalian subjects may include, but are not limited to, humans, non-human primates (e.g., monkeys, chimpanzees, baboons, etc.), dogs, cats, mice, hamsters, rats, horses, cows, pigs, rabbits, sheep and goats. Avian subjects may include, but are not limited to, chickens, turkeys, ducks, geese, quail and pheasant, and birds kept as pets (e.g., parakeets, parrots, macaws, cockatoos, and the like). In particular embodiments, the subject is from an endangered species. In particular embodiments, the subject is a laboratory animal. Human subjects may include neonates, infants, juveniles, adults, and geriatric subjects. In particular embodiments, the subject is male. In particular embodiments, the subject is female.

As used herein, the term “therapeutically effective” refers to provision of some improvement or benefit to the subject. Alternatively stated, a “therapeutically effective amount” is an amount that will provide some alleviation, mitigation, or decrease in at least one clinical symptom in the subject (e.g., in the case of cancer, reduced tumor size, decreased incidence of metastasis, etc.). Those skilled in the art will appreciate that the therapeutic effects need not be complete or curative, as long as some benefit is provided to the subject.

As used herein, the terms “therapeutically effective amount” and “therapeutically acceptable amount” (and grammatical variants thereof) refer to an amount that will elicit a therapeutically useful response in a subject. The therapeutically useful response may provide some alleviation, mitigation, or decrease in at least one clinical symptom in the subject. The terms also include an amount that will prevent or delay at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

As used herein, the terms “treatment,” “treat,” and “treating” refer to reversing, alleviating, delaying the onset of, inhibiting the progress of or preventing a disease or disorder. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

As used herein, the term “treatment effective amount” (and grammatical variants thereof) refers to an amount that is sufficient to provide some improvement or benefit to the subject. Alternatively stated, a “treatment effective amount” is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

The present invention provides compositions useful for the prevention and/or treatment of disease.

In some embodiments, the present invention provides a compound of Formula I

Formula I

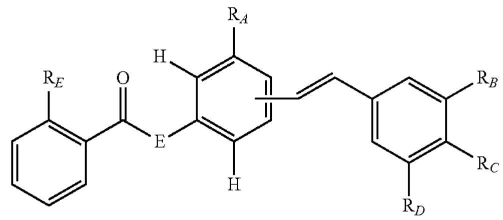

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, — O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C (O)-Me. In some such embodiments, E is —O— and $R_A$ is —OH. In some such embodiments, E is —O— and $R_A$ is —H.

In some embodiments, the present invention provides a compound of Formula IA

Formula IA

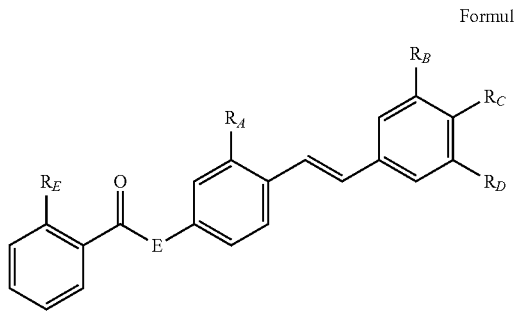

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, =O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C (O)-Me. In some such embodiments, E is —O— and $R_A$ is —OH. In some such embodiments, E is —O— and $R_A$ is —H.

In some embodiments, the present invention provides a compound of Formula IB

Formula IB

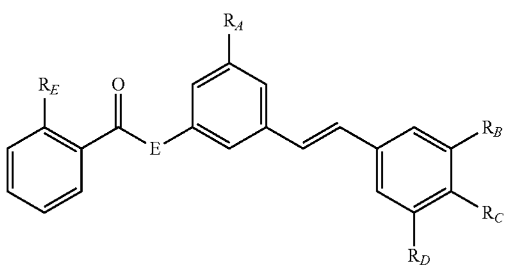

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is j —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C (O)-Me. In some such embodiments, E is —O— and $R_A$ is —OH. In some such embodiments, E is —O— and $R_A$ is —H.

In some embodiments, the present invention provides a compound of Formula II

Formula II or a pharmaceutically acceptable salt or prodrug thereof, wherein each of $R_B$ and $R_D$ is independently —H, —OH or —O—$C_{1-6}$ alkyl; and $R_E$ is —O—C(O)-Me. In some such embodiments, each of $R_B$ and $R_D$ is independently —OH or —O—$C_{1-6}$ alkyl. In some such embodiments, each of $R_B$ and $R_D$ is —OH. In some such embodiments, each of $R_B$ and $R_D$ is —O—$C_{1-6}$ alkyl. In some such embodiments, each of $R_B$ and $R_D$ is independently —O—$C_{1-3}$ alkyl.

In some such embodiments, each of $R_B$ and $R_D$ is —O—$C_{1-3}$ alkyl. In some such embodiments, each of $R_B$ and $R_D$ is —O-Me. In some such embodiments, neither $R_B$ nor $R_D$ is —OMe. In some such embodiments, one of $R_B$ and $R_D$ is —OH and the other is —O—$C_{1-6}$ alkyl. In some such embodiments, one of $R_B$ and $R_D$ is —OH and the other is —OMe, —OEt, —OPr, or —OBu. In some such embodiment each of $R_B$ and $R_D$ independently is —OH, —OMe, —OEt, —OPr, or —OBu. In some such embodiments each of $R_B$ and $R_D$ independently is —OH, —OMe or —OEt.

In some embodiments, the present invention provides a compound of Formula III

Formula III or a pharmaceutically acceptable salt or prodrug thereof, wherein $R_A$ is —H or —OH; $R_C$ is —H, —OH, or —O—$C_{1-6}$ alkyl; and $R_E$ is —OH or O—$C_{1-6}$ acyl. In some such embodiments, $R_C$ is —H, —OH, —OMe, —OEt, —OPr, or —OBu. In some such embodiments, $R_E$ is —OH or O—$C_{1-3}$ acyl. In some such embodiments, $R_E$ is —OH, —O—C(O)-Me, —O—C(O)-Et, —O—C(O)—Pr, or —O—C(O)-Bu. In some such embodiments, each of $R_A$ and $R_C$ is —OH. In some such embodiments, each of $R_A$ and $R_E$ is —OH. In some such embodiments, each of $R_C$ and $R_E$ is —OH. In some such embodiments, $R_A$ is —OH; $R_C$ is —H or —OH; and $R_E$ is —OH or —O—$C_{1-6}$ acyl. In some such embodiments, $R_A$ is —OH; $R_C$ is —H or —OH; and $R_E$ is —OH or O—$C_{1-3}$ acyl. In some such embodiments, $R_E$ is —O—C(O)-Me. In some such embodiments, $R_C$ is —OH and $R_E$ is —O—C(O)-Me, —O—C(O)-Et, —O—C(O)—Pr, —O—C(O)-Bu. In some such embodiments, $R_C$ is —OH and $R_E$ is —O—C(O)-Me. In some embodiments, each of $R_A$ and $R_C$ is —OH and $R_E$ is —O—C(O)Me. In some such embodiments, $R_A$ is —OH; $R_C$ is —H, —OH, —OMe, —OEt, —OPr, or —OBu and $R_E$ is —OH, —O—C(O)-Me, —O—C(O)-Et, —O—C(O)—Pr, or —O—C(O)-Bu. In some such embodiments, $R_A$ is —H; $R_C$ is —OH, or —O—$C_{1-6}$ alkyl; and $R_E$ is —OH or —O—$C_{1-6}$ acyl. In some such embodiments, $R_A$ is —H; $R_C$ is —OH, —OMe, —OEt, —OPr, or —OBu; and $R_E$ is —OH or —O—$C_{1-6}$ acyl.

In some embodiments, the present invention provides a compound of Formula IV

Formula IV

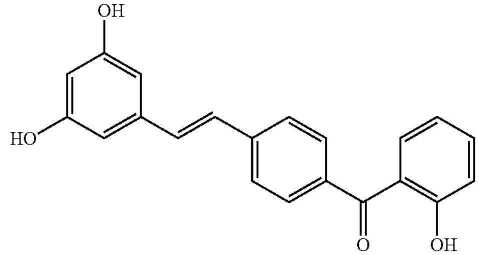

or a pharmaceutically acceptable salt or prodrug thereof.

In some embodiments, the present invention provides a compound of Formula V

Formula V

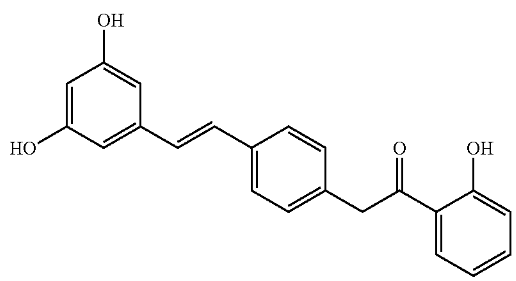

or a pharmaceutically acceptable salt or prodrug thereof.

In some embodiments, the present invention provides a compound of Formula VI

Formula VI

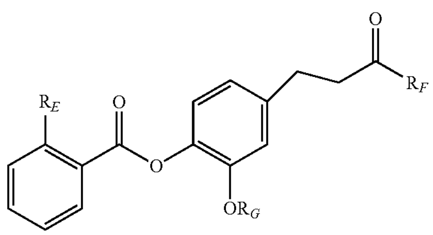

or a pharmaceutically acceptable salt or prodrug thereof, wherein $R_E$ is —H, —OH, or —O—$C_{1-6}$ acyl; $R_F$ is optionally substituted $C_{1-12}$ alkyl or optionally substituted $C_{1-12}$ alkenyl; and $R_G$ is —H or $C_{1-6}$ alkyl. In some such embodiments, $R_E$ is —O—C(O)—$C_{1-3}$ alkyl. In some such embodiments, $R_E$ is —OH, —O—C(O)-Me, —O—C(O)-Et, —O—C(O)—Pr, or —O—C(O)-Bu. In some such embodiments, $R_G$ is —H or -Me. In some such embodiments, $R_E$ is —O—C(O)-Me and $R_G$ is -Me. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is

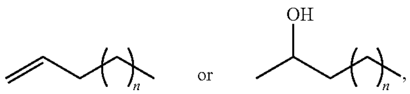

wherein n=3, 5, or 7. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments $R_G$ is -Me; $R_E$ is —OH or —O—C(O)-Me; and $R_F$ is optionally substituted $C_{2-7}$ alkyl or optionally substituted $C_{2-7}$ alkenyl. In some such embodiments, $R_G$ is —H or -Me; $R_E$ is —OH, —O—C(O)-Me, —O—C(O)-Et, —O—C(O)—Pr, or —O—C(O)-Bu; and $R_F$ is:

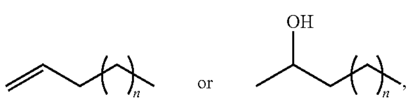

wherein n=3, 5, or 7; in some variations, n=3; in some variations n=5; in some variations n=7.

In some embodiments, the present invention provides a compound of Formula VII

Formula VII

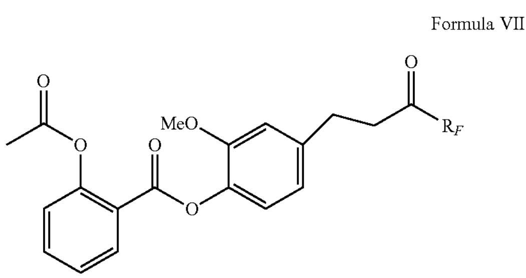

or a pharmaceutically acceptable salt or prodrug thereof, wherein $R_F$ is optionally substituted $C_{1-12}$ alkyl or optionally substituted $C_{1-12}$ alkenyl. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments, $R_F$ is optionally substituted $C_7$ alkyl or optionally substituted $C_7$ alkenyl. In some such embodiments, $R_F$ is optionally substituted $C_9$ alkyl or optionally substituted $C_9$ alkenyl. In some such embodiments, $R_F$ is optionally substituted $C_{11}$ alkyl or optionally substituted $C_1$ alkenyl. In some such embodiments, $R_F$ is

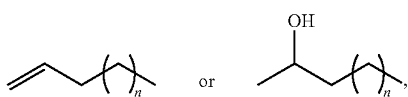

wherein n=3, 5, or 7; in some variations, n=3; in some variations n=5; in some variations n=7.

In some embodiments, the present invention provides a compound comprising a first moiety and a second moiety, wherein the first and second moieties are covalently linked. In some such embodiments, the first moiety is aspirin, an aspirin analog or an aspirin derivative. In some such embodiments, the second moiety is stilbene, an analog or derivative of stilbene, gingerol, an analog or derivative of gingergol, shogaol, an analog or derivative of shogaol, zingerone or an analog or derivative of zingerone. In some such embodiments, the second moiety is not pterostilbene or an analog or derivative thereof. In some such embodiments, the second moiety is not an analog or derivative of pterostilbene. In some such embodiments, the first and second moieties behave in a synergistic manner following administration of the compound to a subject.

Compounds of the present invention may comprise any suitable aspirin derivative or analog, including, but not limited to,

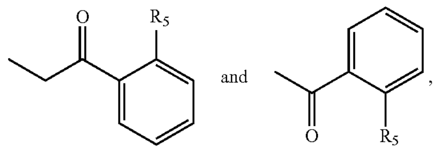

wherein $R_5$ is —OH or —O—$C_{1-6}$ alkyl. In some embodiments, $R_5$ is —OMe, —OEt, —OPr, or —OBu.

Compounds of the present invention may comprise any suitable isomer of stilbene, including (E)-stilbene and (Z)-stilbene.

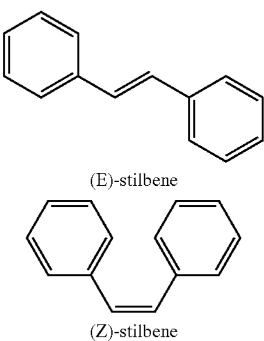

(E)-stilbene (Z)-stilbene

Compounds of the present invention may comprise any suitable stilbene derivative or analog, including, but not limited to, hydroxylated derivatives of stilbene such as resveratrol (3,5,4'-trihydroxy-trans-stilbene), pterostilbene (3,5-dimethoxy-4'-hydroxy-E-stilbene), piceatannol (3',4',3,5-Tetrahydroxy-trans-stilbene) and pinosylvin (trans-3,5-dihydroxystilbene). In some embodiments, the stilbene derivative or analog is a derivative or analog of resveratrol (e.g., alkylated resveratrol derivatives and methylated resveratrol derivatives), a derivative or analog of pterostilbene, a derivative or analog of piceatannol or a derivative or analog of pinosylvin. In some embodiments, the stilbene derivative or analog is an alkylated resveratrol derivative of Formula VIII Formula VIII

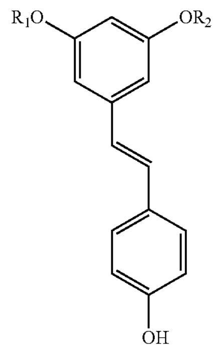

wherein each of $R_1$ and $R_2$ independently is —H or a $C_1$-$C_6$ carbon chain. In some embodiments, the stilbene derivative or analog is a compound of Formula IX Formula IX

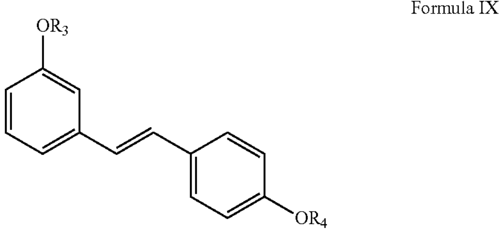

wherein each of $R_3$ and $R_4$ independently is —H or a $C_1$-$C_6$ carbon chain.

Compounds of the present invention may comprise any suitable compound derived from ginger, including, but not limited to, gingerol, shogaol and zingerone.

Compounds of the present invention may comprise any suitable gingerol derivative or analog, including, but not limited to, 8-gingerol and 10-gingerol.

Compounds of the present invention may comprise any suitable shogaol derivative or analog, including, but not limited to, 8-shogaol and 10-shogaol.

Compounds of the present invention may comprise any suitable zingerone derivative or analog, including, but not limited to, rheosmin and quinoline derivatives of zingerone.

Compounds of the present invention may be stable in environments having a pH less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8 or 14.0. In some embodiments, the compound is stable in environments having a pH in the range of about 0.0 to about 7.0, about 0.0 to about 6.0, about 0.0 to about 5.0, about 0.0 to about 4.0, about 0.0 to about 3.5, about 0.0 to about 3.0, about 0.0 to about 2.5, about 0.0 to about 2.0, about 0.0 to about 1.5, about 0.0 to about 1.0, or about 0.0 to about 0.5. In some embodiments, the compound is stable in environments having a pH in the range of about 0.5 to about 7.0, about 0.5 to about 6.0, about 0.5 to about 5.0, about 0.5 to about 4.0, about 0.5 to about 3.5, about 0.5 to about 3.0, about 0.0 to about 2.5, about 0.0 to about 2.0, about 0.5 to about 1.5, or about 0.5 to about 1.0. In some embodiments, the compound is stable in environments having a pH in the range of about 1.0 to about 7.0, about 1.0 to about 6.0, about 1.0 to about 5.0, about 1.0 to about 4.0, about 1.0 to about 3.5, about 1.0 to about 3.0, about 1.0 to about 2.5, about 1.0 to about 2.0, or about 1.0 to about 1.5. In some embodiments, the compound is stable in environments having a pH in the range of about 1.5 to about 7.0, about 1.5 to about 6.0, about 1.5 to about 5.0, about 1.5 to about 4.0, about 1.5 to about 3.5, about 1.5 to about 3.0, about 1.0 to about 2.5, or about 1.0 to about 2.0. In some embodiments, the compound is stable in environments having a pH in the range of about 2.0 to about 7.0, about 2.0 to about 6.0, about 2.0 to about 5.0, about 2.0 to about 4.0, about 2.0 to about 3.5, about 2.0 to about 3.0, or about 0.0 to about 2.5. In some embodiments, the compound is stable in environments having a pH in the range of about 2.5 to about 7.0, about 2.5 to about 6.0, about 2.5 to about 5.0, about 2.5 to about 4.0, about 2.5 to about 3.5, or about 2.5 to about 3.0. In some embodiments, the compound is stable in environments having a pH in the range of about 3.0 to about 7.0, about 3.0 to about 6.0, about 3.0 to about 5.0, about 3.0 to about 4.0, or about 3.0 to about 3.5. In some embodiments, the compound is stable in environments having a pH in the range of about 4.0 to about 7.0, about 4.0 to about 6.0 about 4.0 to about 5.0. In some embodiments, the compound is stable in environments having a pH in the range of about 5.0 to about 7.0, about 5.0 to about 6.0. In some embodiments, the compound is stable in environments having a pH in the range of about 6.0 to about 7.0. In some embodiments, the compound is stable in gastric fluids.

Compounds of the present invention may be stable in environments having a pH greater than about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8 or 13.9.

Compounds of the present invention may not hydrolyze in the stomach.

Compounds of the present invention may be hydrolyzed in vivo to regenerate aspirin (and/or an aspirin derivative or analog) and stilbene/gingerol (and/or a stilbene/gingerol derivative or analog). See FIG. 5. Accordingly, compounds of the present invention may serve as prodrugs of aspirin (and aspirin derivatives and analogs) and stilbene/gingerol (and stilbene/gingerol derivatives and analogs).

Compounds of the present invention may exist as stereoisomers, such as double-bond isomers (i.e., geometric isomers), enantiomers or diastereomers. The chemical structures depicted herein are intended to encompass all possible enantiomers and stereoisomers of the illustrated compounds, including the stereoisomerically pure form (e.g., geometrically pure, enantiomerically pure or diastereomerically pure) and enantiomeric and stereoisomeric mixtures. As will be understood by those skilled in the art, enantiomeric and stereoisomeric mixtures can be resolved into their component enantiomers or stereoisomers using well known separation techniques and/or chiral synthesis techniques.

Compounds of the present invention may exist in several tautomeric forms, including the enol form, the keto form and mixtures thereof. The chemical structures depicted herein are intended to encompass all possible tautomeric forms of the illustrated compounds.

Compounds of the present invention may exist as isotopically labeled compounds, wherein one or more atoms have an atomic mass different from the atomic mass conventionally found in nature. Examples of isotopes that can be incorporated into the compounds of the present invention include, but are not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$. The chemical structures depicted herein are intended to encompass all possible isotopically labeled versions of the compounds of the present invention. Isotopically labeled compounds of the present invention may be used in any suitable method known in the art, including, but not limited to, methods of preventing, diagnosing, monitoring and/or treating a disorder.

Compounds of the present invention may comprise any suitable pharmaceutically acceptable salt, including, but not limited to, acid addition salts and base addition salts. Examples of suitable salts can be found, for example, in STAHL AND WERMUTH, HANDBOOK OF PHARMACEUTICAL SALTS PROPERTIES, SELECTION, AND USE, Wiley-VCH, Weinheim, Germany (2002); and Berge et al., *Pharmaceutical Salts*, J. PHARM. SCI. 66:1-19 (1977). In some embodiments, the pharmaceutically acceptable salt is a disalt. In some embodiments, the pharmaceutically acceptable salt is an L-tartrate salt.

Pharmaceutically acceptable acid addition salts include, but are not limited to, non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Pharmaceutically acceptable acid addition salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of Formulas I, II, III, IV, V, VI, VII and VIII. Also contemplated are the salts of amino acids such as arginate, gluconate, galacturonate, and the like.

Acid addition salts of Formulas I, II, III, IV, V, VI, VII and VIII may be prepared by contacting the free form of the basic compound with a sufficient amount of the desired acid to produce the salt in the conventional manner. The free form may be regenerated by contacting the salt form with a base and isolating the free form in the conventional manner. The free forms may differ from their respective salt forms somewhat in certain physical properties (e.g., solubility in polar solvents), but may otherwise be equivalent to their respective salt forms.

Pharmaceutically acceptable base addition salts may be formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of Formulas I, II, III, IV, V, VI, VII and VIII may be prepared by contacting the free form with a sufficient amount of the desired base to produce the salt in the conventional manner. The free form may be regenerated by contacting the salt form with an acid and isolating the free form in a conventional manner. The free forms may differ from their respective salt forms somewhat in certain physical properties (e.g., solubility in polar solvents), but may otherwise be equivalent to their respective free salt forms.

Compounds of the present invention may comprise any suitable prodrug, including, but not limited to, esterified forms of Formulas I, II, III, IV, V, VI, VII and VIII.

Compounds of the present invention may possess one or more desirable pharmacokinetic and/or physiological properties. In some embodiments, the compound exhibits improved solubility (e.g., aqueous solubility), absorption, metabolism and/or clinical efficacy (as compared to the individual moieties that make up the compound, for example).

Compounds of the present invention may have greater and/or more prolonged therapeutic effects than the individual moieties that make up the compound. For example, administration of a conjugate compound comprising aspirin and gingerol may have a more pronounced anti-tumorigenesis effect than administration of aspirin and gingerol (and/or administration of an aspirin derivative/analog and a gingerol derivative/analog). Accordingly, compositions of the present application may achieve adequate anti-tumor efficacy at a lower dose than that required for the individual moieties that make up the compound.

Compounds of the present invention may have fewer and/or less pronounced adverse effects (e.g., adverse GI effects associated with the administration of aspirin) than the individual moieties that make up the compound. For example, administration of a conjugate compound comprising an aspirin derivative and a stilbene derivative may produce fewer adverse effects than administration of the aspirin derivative and the stilbene derivative (and/or administration of aspirin and stilbene themselves). The use of a sustained-release formulation for delivery of the compound may further reduce any adverse effects.

In some embodiments, the present invention provides a pharmaceutical composition comprising, consisting essentially of or consisting of one or more compounds of the present invention and a pharmaceutically acceptable carrier.

In some embodiments, the present invention provides a pharmaceutical composition comprising, consisting essentially of or consisting of 1) a pharmaceutically acceptable carrier and 2) a compound of Formula I Formula I

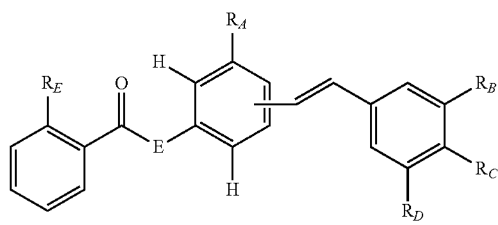

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C (O)-Me. In some such embodiments, E is —O— and $R_A$ is —OH. In some such embodiments, E is —O— and $R_A$ is —H.

In some embodiments, the present invention provides a pharmaceutical composition comprising, consisting essentially of or consisting of 1) a pharmaceutically acceptable carrier and 2) a compound of Formula IA Formula IA

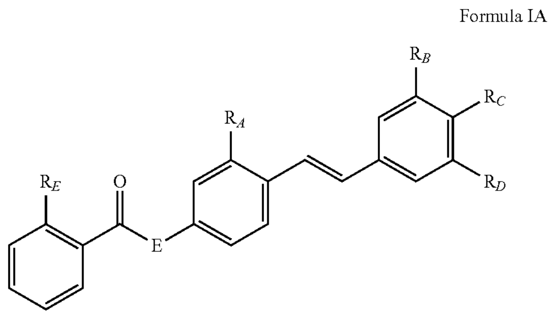

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C(O)-Me. In some such embodiments, E is —O— and $R_A$ is —OH. In some such embodiments, E is —O— and $R_A$ is —H.

In some embodiments, the present invention provides a pharmaceutical composition comprising, consisting essentially of or consisting of 1) a pharmaceutically acceptable carrier and 2) a compound of Formula IB Formula IB

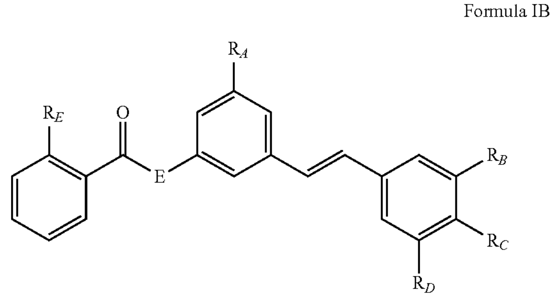

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C(O)-Me. In some such embodiments, E is —O— and $R_A$ is —OH. In some such embodiments, E is —O— and $R_A$ is —H.

In some embodiments, the present invention provides a pharmaceutical composition comprising, consisting essentially of or consisting of 1) a pharmaceutically acceptable carrier and 2) a compound of Formula II Formula II

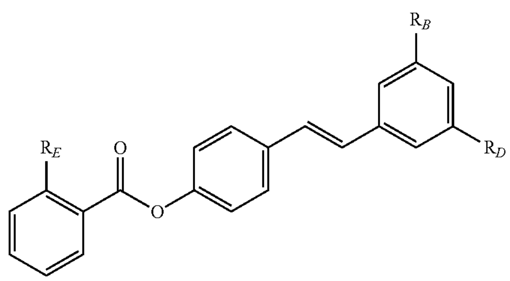

or a pharmaceutically acceptable salt or prodrug thereof, wherein each of $R_B$ and $R_D$ is independently —OH or —O—$C_{1-6}$ alkyl; and $R_E$ is —O—C(O)-Me. In some such embodiments, each of $R_B$ and $R_D$ is independently —OH or —O—$C_{1-6}$ alkyl. In some such embodiments, each of $R_B$ and $R_D$ is —OH. In some such embodiments, each of $R_B$ and $R_D$ is —O—$C_{1-6}$ alkyl. In some such embodiments, each of $R_B$ and $R_D$ is independently —O—$C_{1-3}$ alkyl. In some such embodiments, each of $R_B$ and $R_D$ is —O—$C_{1-3}$ alkyl. In some such embodiments, each of $R_B$ and $R_D$ is —O-Me. In some such embodiments, neither $R_B$ nor $R_D$ is —OMe. In some such embodiments, one of $R_B$ and $R_D$ is —OH and the other is —O—$C_{1-6}$ alkyl. In some such embodiments, one of $R_B$ and $R_D$ is —OH and the other is —OMe, —OEt, —OPr, or —OBu. In some such embodiment each of $R_B$ and $R_D$ independently is —OH, —OMe, —OEt, —OPr, or —OBu. In some such embodiments each of $R_B$ and $R_D$ independently is —OH, —OMe or —OEt.

In some embodiments, the present invention provides a pharmaceutical composition comprising, consisting essentially of or consisting of 1) a pharmaceutically acceptable carrier and 2) a compound of Formula III Formula III

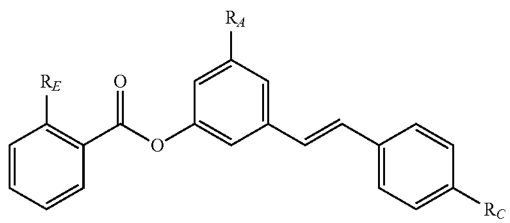

or a pharmaceutically acceptable salt or prodrug thereof, wherein $R_A$ is —H or —OH; $R_C$ is —H, —OH, or —O—$C_{1-6}$ alkyl; and $R_E$ is —OH or O—$C_{1-6}$ acyl. In some such embodiments, $R_C$ is —H, —OH, —OMe, —OEt, —OPr, or —OBu. In some such embodiments, $R_E$ is —OH or O—$C_{1-3}$ acyl.

In some such embodiments, $R_E$ is —OH, —O—C(O)-Me, —O—C(O)-Et, —O—C(O)—Pr, or —O—C(O)-Bu. In some such embodiments, each of $R_A$ and $R_C$ is —OH. In some such embodiments, each of $R_A$ and $R_E$ is —OH. In some such embodiments, each of $R_C$ and $R_E$ is —OH. In some such embodiments, $R_A$ is —OH; $R_C$ is —H or —OH; and $R_E$ is —OH or —O—$C_{1-6}$ acyl. In some such embodiments, $R_A$ is —OH; $R_C$ is —H or —OH; and $R_E$ is —OH or O—$C_{1-3}$ acyl. In some such embodiments, $R_E$ is —O—C(O)-Me. In some such embodiments, $R_C$ is —OH and $R_E$ is —O—C(O)-Me, —O—C(O)-Et, —O—C(O)—Pr, —O—C(O)-Bu. In some such embodiments, $R_C$ is —OH and $R_E$ is —O—C(O)-Me. In some embodiments, each of $R_A$ and $R_C$ is —OH and $R_E$ is —O—C(O)Me. In some such embodiments, $R_A$ is —OH; $R_C$ is —H, —OH, —OMe, —OEt, —OPr, or —OBu and $R_E$ is —OH, —O—C(O)-Me, —O—C(O)-Et, —O—C(O)—Pr, or —O—C(O)-Bu. In some such embodiments, $R_A$ is —H; $R_C$ is —OH, or —O—$C_{1-6}$ alkyl; and $R_E$ is —OH or —O—$C_{1-6}$ acyl. In some such embodiments, $R_A$ is —H; $R_C$ is —OH, —OMe, —OEt, —OPr, or —OBu; and $R_E$ is —OH or —O—$C_{1-6}$ acyl.

In some embodiments, the present invention provides a pharmaceutical composition comprising, consisting essentially of or consisting of 1) a pharmaceutically acceptable carrier and 2) a compound of Formula IV Formula IV

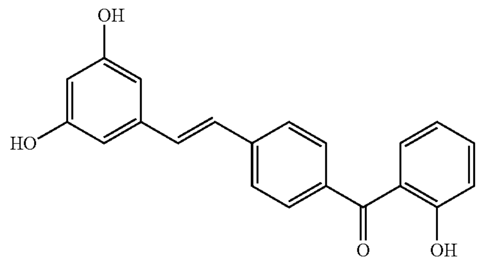

or a pharmaceutically acceptable salt or prodrug thereof.

In some embodiments, the present invention provides a pharmaceutical composition comprising, consisting essentially of or consisting of 1) a pharmaceutically acceptable carrier and 2) a compound of Formula V Formula V

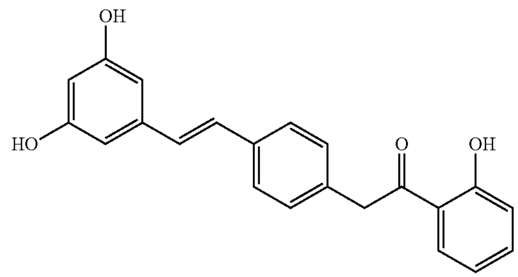

or a pharmaceutically acceptable salt or prodrug thereof.

In some embodiments, the present invention provides a pharmaceutical composition comprising, consisting essentially of or consisting of 1) a pharmaceutically acceptable carrier and 2) a compound of Formula VI Formula VI

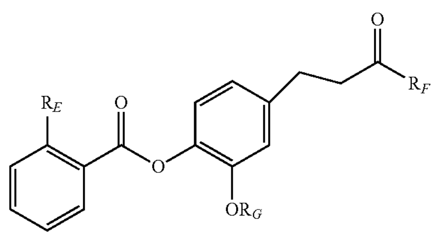

or a pharmaceutically acceptable salt or prodrug thereof, wherein $R_E$ is —H, —OH, or —O—$C_{1-6}$ acyl; $R_F$ is optionally substituted $C_{1-12}$ alkyl or optionally substituted $C_{1-12}$ alkenyl; and $R_G$ is —H or $C_{1-6}$ alkyl. In some such embodiments, $R_E$ is —O—C(O)—$C_{1-3}$ alkyl. In some such embodiments, $R_E$ is —OH, —O—C(O)-Me, —O—C(O)-Et, —O—C(O)—Pr, or —O—C(O)-Bu. In some such embodiments, $R_G$ is —H or -Me. In some such embodiments, $R_E$ is —O—C(O)-Me and $R_G$ is -Me. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is

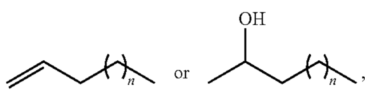

wherein n=3, 5, or 7. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments $R_G$ is -Me; $R_E$ is —OH or —O—C(O)-Me; and $R_F$ is optionally substituted $C_{2-7}$ alkyl or optionally substituted $C_{2-7}$ alkenyl. In some such embodiments, $R_G$ is —H or -Me; $R_E$ is —OH, —O—C(O)-Me, —O—C(O)-Et, —O—C(O)—Pr, or —O—C(O)-Bu; and $R_F$ is:

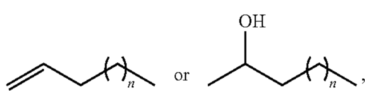

wherein n=3, 5, or 7; in some variations, n=3; in some variations n=5; in some variations n=7.

In some embodiments, the present invention provides a pharmaceutical composition comprising, consisting essentially of or consisting of 1) a pharmaceutically acceptable carrier and 2) a compound of Formula VII Formula VII

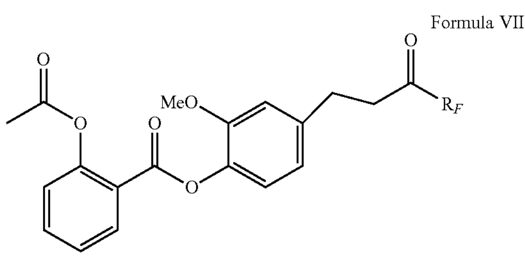

or a pharmaceutically acceptable salt or prodrug thereof, wherein $R_F$ is optionally substituted $C_{1-12}$ alkyl or optionally substituted $C_{1-12}$ alkenyl. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments, $R_F$ is optionally substituted $C_7$ alkyl or optionally substituted $C_7$ alkenyl. In some such embodiments, $R_F$ is optionally substituted $C_9$ alkyl or optionally substituted $C_9$ alkenyl. In some such embodiments, $R_F$ is optionally substituted $C_{11}$ alkyl or optionally substituted $C_{11}$ alkenyl. In some such embodiments, $R_F$ is

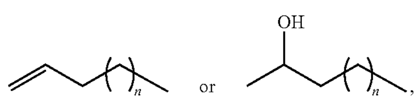

wherein n=3, 5, or 7; in some variations, n=3; in some variations n=5; in some variations n=7.

The concentration of the compound(s) in the pharmaceutical composition may vary widely (i.e., from less than about 0.05% to about 90% or more by weight) in accordance with the particular mode of administration, the disease(s)/disorder(s)/symptom(s) being treated, the age/weight of the subject, etc.

In some such embodiments, the pharmaceutical composition comprises a unit dose comprising, consisting essentially of or consisting of a compound of the present invention and a pharmaceutically acceptable carrier. The unit dose may be from about 0.5 to about 500 mg/kg, about 0.5 to about 450 mg/kg, about 0.5 to about 400 mg/kg, about 0.5 to about 350 mg/kg, about 0.5 to about 300 mg/kg, about 0.5 to about 250 mg/kg, about 0.5 to about 200 mg/kg, about 0.5 to about 150 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 0.5 to about 5 mg/kg; about 1 to about 500 mg/kg, about 1 to about 450 mg/kg, about 1 to about 400 mg/kg, about 1 to about 350 mg/kg, about 1 to about 300 mg/kg, about 1 to about 250 mg/kg, about 1 to about 200 mg/kg, about 1 to about 150 mg/kg, about 1 to about 100 mg/kg, about 1 to about 50 mg/kg, about 1 to about 25 mg/kg, about 1 to about 20 mg/kg, about 1 to about 15 mg/kg, about 1 to about 10 mg/kg, about 1 to about 5 mg/kg, about 2 to about 500 mg/kg, about 2 to about 450 mg/kg, about 2 to about 400 mg/kg, about 2 to about 350 mg/kg, about 2 to about 300 mg/kg, about 2 to about 250 mg/kg, about 2 to about 200 mg/kg, about 2 to about 150 mg/kg, about 2 to about 100 mg/kg, about 2 to about 50 mg/kg, about 2 to about 25 mg/kg, about 2 to about 20 mg/kg, about 2 to about 15 mg/kg, about 2 to about 10 mg/kg, about 2 to about 5 mg/kg, 3 to about 500 mg/kg, about 3 to about 450 mg/kg, about 3 to about 400 mg/kg, about 3 to about 350 mg/kg, about 3 to about 300 mg/kg, about 3 to about 250 mg/kg, about 3 to about 200 mg/kg, about 3 to about 150 mg/kg, about 3 to about 100 mg/kg, about 3 to about 50 mg/kg, about 3 to about 25 mg/kg, about 3 to about 20 mg/kg, about 3 to about 15 mg/kg, about 3 to about 10 mg/kg, or about 3 to about 5 mg/kg of a composition of the present invention (e.g., a compound of the present invention). In some embodiments, the unit dose is at least about 1 μg/kg, 2 μg/kg, 3 μg/kg, 4 μg/kg, 5 μg/kg, 10 μg/kg, 15 μg/kg, 20 μg/kg, 30 g/kg, 40 μg/kg, 50 μg/kg, 60 μg/kg, 70 μg/kg, 80 μg/kg, 90 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 250 mg/kg, 300 mg/kg, 350 mg/kg, 400 mg/kg, 450 mg/kg, 500 mg/kg, 1000 mg/kg or more of a composition of the present invention (e.g., a compound of the present invention).

Pharmaceutical compositions of the present invention may comprise any suitable pharmaceutical carrier moiety, including, but not limited to, phosphate buffered saline and isotonic saline solution. Other examples of pharmaceutically acceptable carriers may be found, for example, in ANSEL'S PHARMACEUTICAL DOSAGE FORMS AND DRUG DELIVERY SYSTEMS (9th Ed., Lippincott Williams and Wilkins (2010)), PHARMACEUTICAL SCIENCES (18th Ed., Mack Publishing Co. (1990) or REMINGTON: THE SCIENCE AND PRACTICE OF PHARMACY (21st Ed., Lippincott Williams & Wilkins (2005)).

Pharmaceutical compositions of the present invention may comprise any suitable diluent or excipient, including, but not limited to, those set forth in ANSEL'S PHARMACEUTICAL DOSAGE FORMS AND DRUG DELIVERY SYSTEMS (9th Ed., Lippincott Williams and Wilkins (2010)), HANDBOOK OF PHARMACEUTICAL EXCIPIENTS (6th Ed., American Pharmaceutical Association (2009)) and REMINGTON: THE SCIENCE AND PRACTICE OF PHARMACY (21st Ed., Lippincott Williams & Wilkins (2005)). In some embodiments, the composition comprises one or more pharmaceutically acceptable diluents and/or one or more pharmaceutically acceptable excipients.

Pharmaceutical compositions of the present invention may comprise any suitable auxiliary substance, including, but not limited to, pH adjusting and/or buffering agents, tonicity adjusting and/or buffering agents and lipid-protective agents that protect lipids against free-radical and lipid-peroxidative damages (e.g., alpha-tocopherol and water-soluble iron-specific chelators, such as ferrioxamine).

Pharmaceutical compositions of the present invention may comprise at least one supplemental agent. In some embodiments, the at least one supplemental agent comprises another compound of the present invention. In some embodiments, the at least one supplemental agent comprises an antitumor alkylating agent, an antitumor antimetabolite, an antitumor antibiotics, a plant-derived antitumor agent, an antitumor organoplatinum compound, an antitumor campthotecin derivative, an antitumor tyrosine kinase inhibitor, a monoclonal antibody, an interferon, a biological response modifier, a hormonal anti-tumor agent, an angiogenesis inhibitor, a differentiating agent or a pharmaceutically acceptable salt or prodrug of any of the foregoing.

Pharmaceutical compositions of the present invention may be in any form suitable for the intended method of administration and may be prepared according to any suitable method.

Pharmaceutical compositions for oral use may be presented as tablets, troches, lozenges, aqueous or oil suspensions, dispersible powders or granules, emulsions, hard or soft capsules, syrups and/or elixirs. Such compositions may comprise one or more sweetening agents, flavoring agents, coloring agents and/or preserving agents.

Formulation for oral use may be tablets containing a compound of the present invention in admixture with one or more pharmaceutically acceptable excipients. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be presented as hard gelatin capsules where the compound of the present invention is mixed with an inert solid diluent, for example calcium phosphate or kaolin, or as soft gelatin capsules wherein the compound of the present invention is mixed with water or an oil medium, such as peanut oil, liquid paraffin or olive oil Aqueous suspensions of the application contain the compound of the present invention in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the compound of the present invention in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the application suitable for preparation of an aqueous suspension by the addition of water provide the compound of the present invention in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

Pharmaceutical compositions of the present invention may be in the form of an oil-in-water emulsion. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

Pharmaceutical compositions of the present invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

As noted above, formulations of the present invention suitable for oral-administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Pharmaceutical compositions of the present invention may be in immediate-release formulations. A variety of known methods and materials may be used to bring about the immediate release. For instance, placing the compound of the present invention along an exterior of a tablet (e.g., coating the exterior or formulating the outer layer with the agent) and/or combined with forming a tablet by compressing the powder using low compaction can produce immediate-release of the compound of the present invention from the composition.

Pharmaceutical compositions of the present invention may be in controlled-release and/or sustained-release formulations. Pharmaceutical compositions of the present invention may comprise one or more carriers that protect the compound of the present invention against rapid elimination from the body, such as time-release formulations or coatings. Such carriers include controlled-release formulations, including, for example, microencapsulated delivery systems. Compounds of the present invention can be included in the pharmaceutically acceptable carrier in amounts sufficient to treat an individual. The controlled-release form can be in an amount that is effective to protect the compound of the present invention from rapid elimination from the body, or to provide a sustained release or dosage, such as between about 1 μg/kg/min to about 500 μg/kg/min, or alternately between about 2 μg/kg/min to about 250 μg/kg/min. Generally the controlled release dosage form provides less than 100 μg/kg/min, less than 50 μg/kg/min or even less than 10 μg/kg/min.

In some embodiments, the pharmaceutical composition is in oral dosage form and comprises a matrix that includes a controlled-release material. In certain embodiments, the matrix is compressible into a tablet and can be optionally overcoated with a coating that can control the release of the compound of the present invention from the composition. In this embodiment, the compound of the present invention is maintained within a therapeutic range over an extended period of time. In certain alternate embodiments, the matrix is encapsulated.

Tablets or capsules containing a composition of the present application can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be delayed in release. For controlled extended release, the capsule can also have micro drilled holes.

A coating comprising an initial dose or first dose of a compound of the present invention in immediate-release form can be added to the outside of a controlled-release tablet core comprising a second dose of a compound of the present invention to produce a final dosage form. Such a coating can be prepared by admixing the first dosage with polyvinylpyrrolidone (PVP) 29/32 or hydroxypropyl methylcellulose (HPMC) and water/isopropyl alcohol and triethyl acetate. Such an immediate-release coating can be spray coated onto the tablet cores. The immediate-release coating can also be applied using a press-coating process with a blend consisting of 80% by weight promethazine and 20% by weight of lactose and hydroxypropyl methylcellulose type 2910. Press-coating techniques are known in the art.

The immediate-release or controlled-release dosage forms of the present invention can also take the form of a multilayer tablet, such as a bi-layered tablet, which comprises a first layer and a second layer. In a further aspect of the bi-layered tablet, the first layer is an immediate release layer and/or the second layer is a controlled-release layer. For example, a multilayered tablet can comprise at least one immediate release layer comprising an amount of a compound of the present invention and at least one controlled release layer which comprises an amount of a compound of the present invention. The controlled release layer may provide sustained release of a compound of the present invention, for a period of time. Alternatively, the immediate release layer and the controlled released layer may provide sustained release of a compound of the present invention, but at different dosage amounts.

The immediate-release or controlled release dosage forms of the present invention can also take the form of pharmaceutical particles manufactured by a variety of methods, including but not limited to high-pressure homogenization, wet or dry ball milling, or small particle precipitation. Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size. These dosage forms can include immediate-release particles in combination with controlled-release particles in a ratio sufficient useful for delivering the desired dosages of the compound of the present invention.

In another aspect of the present application, the components are released from a multi-layered tablet that comprises at least a first layer, a second layer and a third layer. Wherein, the layers containing the compound of the present invention can be optionally separated by one or more layers of inert materials. In one embodiment the layers containing a compound of the present invention have similar rates of release (e.g., all are immediate-release or all are controlled-release). In an alternative embodiment the layers have different rates of release. In this aspect at least one layer is an immediate release layer and at least one layer is a controlled release layer.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for topical administration in the mouth include lozenges comprising the compound of the present invention in a flavored base, usually sucrose and acacia or tragacanth; pastilles comprising the compound of the present invention in an inert base such as gelatin and glycerin, or sucrose and acacia; and mouthwashes comprising the compound of the present invention in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the compound of the present invention such carriers as are known in the art to be appropriate.

Transdermal delivery systems manufactured as an adhesive disc or patch that slowly releases the active ingredient for percutaneous absorption may be used. To this end, permeation enhancers may be used to facilitate transdermal penetration of the active agent. For example, for transdermal administration, the compound of the present invention may be combined with skin penetration enhancers, such as propylene glycol, polyethylene glycol, isopropanol, ethanol, oleic acid, N-methylpyrrolidone, dimethyl sulfoxide, and the like, which increase the permeability of the skin to the compound of the present invention, and permit it to penetrate through the skin and into the bloodstream. The compound of the present invention may also be combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The compound of the present invention may be administered transdermally to achieve a local concentration of the active agent or to achieve systemic administration of the active agent.

Generally speaking, transdermal drug delivery systems are commonly either reservoir-type or matrix-type devices. Both types of devices include a backing layer that forms the outer surface of the finished transdermal device and which is exposed to the environment during use, and a release liner or protective layer that forms the inner surface and which covers the adhesive means for affixing the devices to the skin or mucosa of a user. The release liner or protective layer is removed prior to application, exposing the adhesive means which is typically a pressure-sensitive adhesive. The active agent is located between the release liner and backing layer, usually solubilized or dispersed in a solvent or carrier composition. In some embodiments, the outer surface of the transdermal device (e.g., patch) is adapted to associate with a second component, such as a heating compartment (e.g., electrical or chemical means for providing controlled and consistent increase in temperature).

Compositions of the present invention may be used to prevent, diagnose, monitor and/or treat any suitable disorder, including, but not limited to, cancer. In some embodiments, the disorder is a gastrointestinal cancer, such as an anal cancer, an esophageal cancer, a stomach cancer, a liver cancer, a gallbladder cancer, a pancreatic cancer, a colon cancer or a rectal cancer. In some embodiments, the disorder is lung cancer. In some embodiments, the disorder is a metastatic disorder (e.g., metastatic cancer).

Compositions of the present invention may target one or more biological targets that are relevant to the prevention and/or treatment of cancer.

Compositions of the present invention may be used in combination with at least one supplemental agent. In some embodiments, the at least one supplemental agent comprises a therapeutic agent such as an antitumor alkylating agent, an antitumor antimetabolite, an antitumor antibiotics, a plant-derived antitumor agent, an antitumor organoplatinum compound, an antitumor campthotecin derivative, an antitumor tyrosine kinase inhibitor, a monoclonal antibody, an interferon, a biological response modifier, a hormonal anti-tumor agent, an angiogenesis inhibitor, an anti-metastatic agent, a differentiating agent, a chemotherapeutic agent, a chemopreventative agent, a gene therapy agent, an enzymatic inhibitor or a pharmaceutically acceptable salt or prodrug of any of the foregoing. The composition(s) and the supplemental agent can act additively or, more preferably, synergistically.

In some embodiments, the composition may be used in combination with surgery, radiation therapy, chemotherapy, gene therapy, RNA therapy, adjuvant therapy, immunotherapy, nanotherapy or a combination thereof.

Compositions of the present invention may be formulated so as to be suitable for administration via any known method, including, but not limited to, oral, parenteral (e.g., intraarterial, intravenous (i.v.), subcutaneous, intramuscular and intrathecal), intraperitoneal (i.p.), intrarectal, intravaginal, intranasal, intragastric, intratracheal, sublingual, transcutaneous, intrapulmonary and topical administration. In some embodiments, the composition is formulated for oral, parenteral, topical or rectal administration. In some embodiments, the composition is formulated for administration via inhalation (e.g., as a spray or powder). In some embodiments, the composition is formulated for depot administration.

Compositions of the present invention may be administered intravenously or by catheter-based techniques, or a combination thereof, with or without associated delivery devices (i.e., pumps). For example, a pharmaceutical composition of the present invention can be administered intravenously, in or associated with cardioplegia solutions, via local delivery procedures including direct injection into grafts or native arteries, and via perfusion-assisted techniques.

Compositions of the present application can be infused intravenously, while other therapeutically active agents are delivered to the target organ selectively, or both therapies can be delivered by either intravenous or intravascular selective administration.

The present invention provides methods of producing and using compounds of the present invention.

In some embodiments, the present invention provides a method of producing a compound of the present invention, said method comprising, consisting essentially of or consisting of conjugating a first moiety and a second moiety, wherein the first moiety is aspirin, an aspirin analog or an aspirin derivative and the second moiety is stilbene (1,2-diphenylethene), an analog or derivative of stilbene, gingerol (6-gingerol; 5-hydroxy-1-(4-hydroxy-3-methoxyphenyl)-3-decanone), an analog derivative of ginergol, shogaol (6-shogaol; 1-(4-Hydroxy-3-methoxyphenyl)dec-4-en-3-one), an analog or derivative of shogaol, zingerone (4-(4-hydroxy-3-methoxyphenyl)-2-butanone) or an analog or derivative of zingerone.

Any suitable aspirin derivative or analog may be used to produce compounds of the present invention, including, but not limited to,

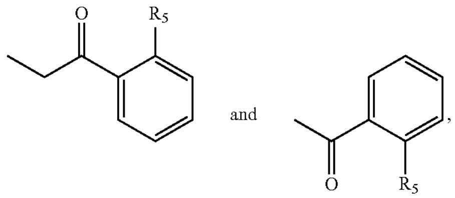

wherein $R_5$ is —OH or —O—$C_{1-6}$ alkyl. In some embodiments, $R_5$ is —OMe, —OEt, —OPr, or —OBu.

Any suitable isomer of stilbene may be used to produce compounds of the present invention, including (E)-stilbene and (Z)-stilbene.

(E)-stillbene (Z)-stilbene

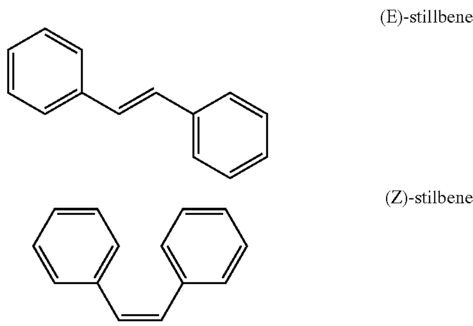

Any suitable stilbene derivative or analog may be used to produce compounds of the present invention, including, but not limited to, hydroxylated derivatives of stilbene such as resveratrol, pterostilbene, piceatannol and pinosylvin. In some embodiments, the stilbene derivative or analog is a derivative or analog of resveratrol (e.g., alkylated resveratrol derivatives and methylated resveratrol derivatives), a derivative or analog of pterostilbene, a derivative or analog of piceatannol or a derivative or analog of pinosylvin. In some embodiments, the stilbene derivative or analog is an alkylated resveratrol derivative of Formula IX Formula IX

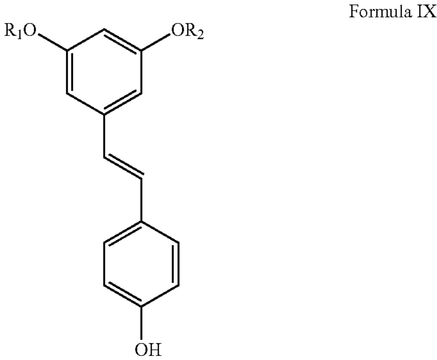

wherein each of $R_1$ and $R_2$ independently is —H or a $C_1$-$C_6$ carbon chain. In some embodiments, the stilbene derivative or analog is a compound of Formula X Formula X

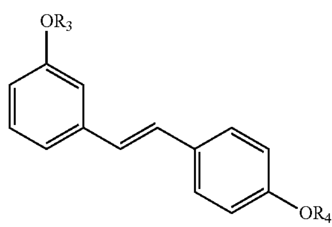

wherein each of $R_3$ and $R_4$ independently is —H or a $C_1$-$C_6$ carbon chain.

The present invention provides methods of 1) preventing, diagnosing, monitoring and/or treating a disorder in a subject in need thereof, 2) reducing one or more adverse effects associated with the treatment of a disorder and/or 3) increasing therapeutic efficacy in the treatment of a disorder.

In some embodiments, the method comprises, consists essentially of or consists of administering to said subject a therapeutically effective amount of a composition of the present invention. In some such embodiments, the therapeutically effective amount comprises a prevention effective amount. In some embodiments, the therapeutically effective amount comprises a treatment effective amount.

In some embodiments, the method comprises, consists essentially of or consists of administering to said subject a therapeutically effective amount of a compound of Formula I Formula I

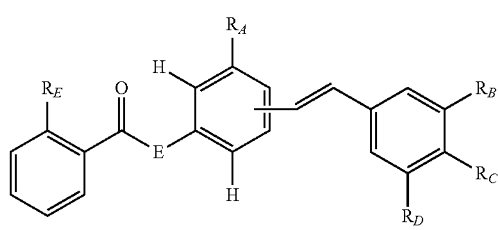

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or —O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, Re and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C (O)-Me. In some such embodiments, E is —O— and $R_A$ is —OH. In some such embodiments, E is —O— and $R_A$ is —H.

In some embodiments, the method comprises, consists essentially of or consists of administering to said subject a therapeutically effective amount of a compound of Formula Formula IA

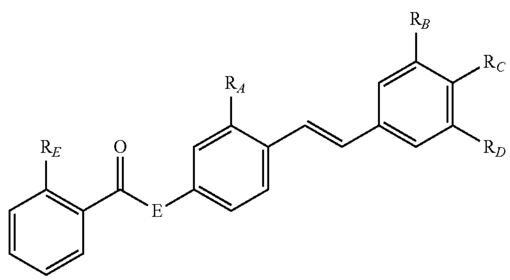

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or —O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C(O)-Me. In some such embodiments, E is —O— and $R_A$ is —OH. In some such embodiments, E is —O— and $R_A$ is —H.

In some embodiments, the method comprises, consists essentially of or consists of administering to said subject a therapeutically effective amount of a compound of Formula IB Formula IB

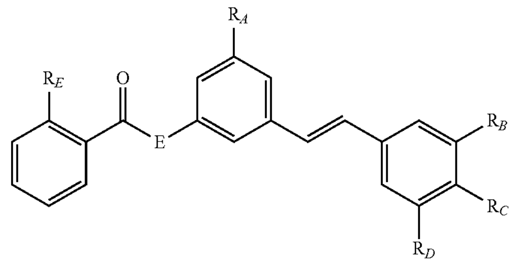

or a pharmaceutically acceptable salt or prodrug thereof, wherein E is —C—, —O—, —S— or is absent; each of $R_A$ and $R_C$ is independently —H or —OH; each of $R_B$ and $R_D$ is independently —H, —OH or —O—$C_{1-6}$ alkyl; and $R_E$ is —OH or —O—$C_{1-6}$ acyl. In some such embodiments, E is —O—; each of $R_A$ and $R_C$ is independently —H or —OH; each of $R_D$ and $R_B$ is independently —H, —OH or —O—$C_{1-6}$ alkyl; and $R_E$ is —H, —OH or —O—$C_{1-6}$ acyl. In some such embodiments, one of $R_B$ and $R_D$ is —H and the other is —OH or —O—$C_{1-6}$ alkyl. In some such embodiments, $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —C—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is —O—; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, E is absent; one of $R_B$ and $R_D$ is —H and the other is —OH or —O—$C_{1-6}$ alkyl; and $R_E$ is —OH, —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu. In some such embodiments, $R_E$ is —O—C(O)-Me, —O—C(O)-Et, —O—C(O)—Pr, or —O—C(O)-Bu. In some such embodiments, one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —C—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is —O—; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, E is absent; one of $R_B$ and $R_D$ is —H and the other is —OH, —OMe, —OEt, —OPr, or —OBu; and $R_E$ is —O—C(O)-Me, —O—C(O)-Et, —O—C(O)—Pr, or —O—C(O)-Bu. In some such embodiments, at least two of $R_B$, $R_C$ and $R_D$ are —OH. In some such embodiments, $R_E$ is —OH and at least two of $R_B$, $R_C$ and $R_D$ are —OH. In some such embodiments, at least two of $R_B$, $R_C$ and $R_D$ are —OH. In some such embodiments, E is —C— and at least two of $R_B$, $R_C$ and $R_D$ are —OH. In some such embodiments, E is —O— and at least two of $R_B$, $R_C$ and $R_D$ are —OH. In some such embodiments, E is absent and at least two of $R_B$, $R_C$ and $R_D$ are —OH. In some such embodiments, E is —C—; $R_E$ is —OH and at least two of $R_B$, $R_C$ and $R_D$ are —OH. In some such embodiments, E is —O—; $R_E$ is —OH and at least two of $R_B$, $R_C$ and $R_D$ are —OH. In some such embodiments, E is absent; $R_E$ is —OH and at least two of $R_B$, $R_C$ and $R_D$ are —OH. In some such embodiments, neither $R_B$ nor $R_D$ is —OMe. In some such embodiments, each of $R_B$ and $R_D$ is independently —H, —OH. In some such embodiments, $R_E$ is —O—C(O)-Me. In some such embodiments, each of $R_B$ and $R_D$ is independently —H, —OH, or —OMe; and $R_E$ is —O—C(O)-Me. In some such embodiments, E is —C—; each of $R_B$ and $R_D$ is independently —H, —OH, or —OMe; and $R_E$ is —O—C(O)-Me. In some such embodiments, E is —O—; each of $R_B$ and $R_D$ is independently —H, —OH, or —OMe; and $R_E$ is —O—C(O)-Me. In some such embodiments, E is absent; each of $R_B$ and $R_D$ is independently —H, —OH, or —OMe; and $R_E$ is —O—C(O)-Me. In some such embodiments, E is —O— and $R_A$ is —OH. In some such embodiments, E is —O— and $R_A$ is —H.

In some embodiments, the method comprises, consists essentially of or consists of administering to said subject a therapeutically effective amount of a compound of Formula II Formula II

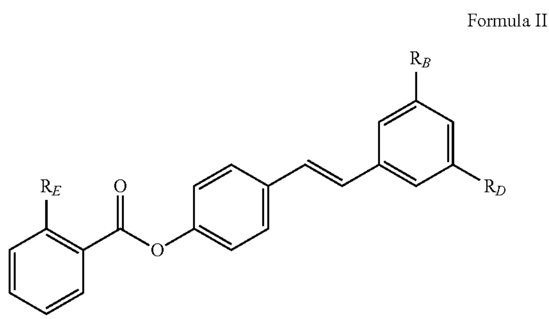

or a pharmaceutically acceptable salt or prodrug thereof, wherein each of $R_B$ and $R_D$ is independently —OH or —O—$C_{1-6}$ alkyl; and $R_E$ is —O—C(O)-Me. In some such embodiments, each of $R_B$ and $R_D$ is independently —OH or —O—$C_{1-6}$ alkyl. In some such embodiments, each of $R_B$ and $R_D$ is —OH. In some such embodiments, each of $R_B$ and $R_D$ is —O—$C_{1-6}$ alkyl. In some such embodiments, each of $R_B$ and $R_D$ is independently —O—$C_{1-3}$ alkyl. In some such embodiments, each of $R_B$ and $R_D$ is —O—$C_{1-3}$ alkyl. In some such embodiments, each of $R_B$ and $R_D$ is —O-Me. In some such embodiments, neither $R_B$ nor $R_D$ is —OMe. In some such embodiments, one of $R_B$ and $R_D$ is —OH and the other is —O—$C_{1-6}$ alkyl. In some such embodiments, one of $R_B$ and $R_D$ is —OH and the other is —OMe, —OEt, —OPr, or —OBu. In some such embodiment each of $R_B$ and $R_D$ independently is —OH, —OMe, —OEt, —OPr, or —OBu. In some such embodiments each of $R_B$ and $R_D$ independently is —OH, —OMe or —OEt.

In some embodiments, the method comprises, consists essentially of or consists of administering to said subject a therapeutically effective amount of a compound of Formula III Formula III

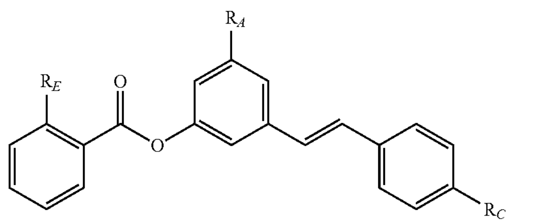

or a pharmaceutically acceptable salt or prodrug thereof, wherein $R_A$ is —H or —OH; $R_C$ is —H, —OH, or —O—$C_{1-6}$ alkyl; and $R_E$ is —OH or —O—$C_{1-6}$ acyl. In some such embodiments, $R_C$ is —H, —OH, —OMe, —OEt, —OPr, or —OBu. In some such embodiments, $R_E$ is —OH or O—$C_{1-3}$ acyl.

In some such embodiments, $R_E$ is —OH, —O—C(O)-Me, —O—C(O)-Et, —O—C(O)—Pr, or —O—C(O)-Bu. In some such embodiments, each of $R_A$ and $R_C$ is —OH. In some such embodiments, each of $R_A$ and $R_E$ is —OH. In some such embodiments, each of $R_C$ and $R_E$ is —OH. In some such embodiments, $R_A$ is —OH; $R_C$ is —H or —OH; and $R_E$ is —OH or —O—$C_{1-6}$ acyl. In some such embodiments, $R_A$ is —OH; $R_C$ is —H or —OH; and $R_E$ is —OH or O—$C_{1-3}$ acyl. In some such embodiments, $R_E$ is —O—C(O)-Me. In some such embodiments, $R_C$ is —OH and $R_E$ is —O—C(O)-Me, —O—C(O)-Et, —O—C(O)—Pr, —O—C(O)-Bu. In some such embodiments, $R_C$ is —OH and $R_E$ is —O—C(O)-Me. In some embodiments, each of $R_A$ and $R_C$ is —OH and $R_E$ is —O—C(O)Me. In some such embodiments, $R_A$ is —OH; $R_C$ is —H, —OH, —OMe, —OEt, —OPr, or —OBu and $R_E$ is —OH, —O—C(O)-Me, —O—C(O)-Et, —O—C(O)—Pr, or —O—C(O)-Bu. In some such embodiments, $R_A$ is —H; $R_C$ is —OH, or —O—$C_{1-6}$ alkyl; and $R_E$ is —OH or —O—$C_{1-6}$ acyl. In some such embodiments, $R_A$ is —H; $R_C$ is —OH, —OMe, —OEt, —OPr, or —OBu; and $R_E$ is —OH or —O—$C_{1-6}$ acyl.

In some embodiments, the method comprises, consists essentially of or consists of administering to said subject a therapeutically effective amount of a compound of Formula IV Formula IV

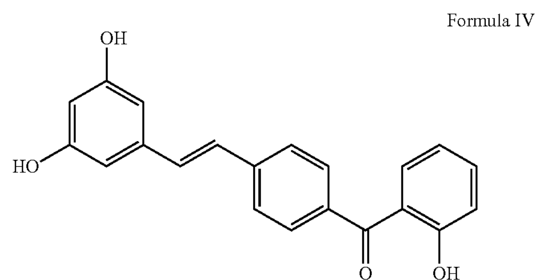 [SMILES: O=C(c1ccc(/C=C/c2cc(O)cc(O)c2)cc1)c1ccccc1O]

or a pharmaceutically acceptable salt or prodrug thereof.

In some embodiments, the method comprises, consists essentially of or consists of administering to said subject a therapeutically effective amount of a compound of Formula V Formula V

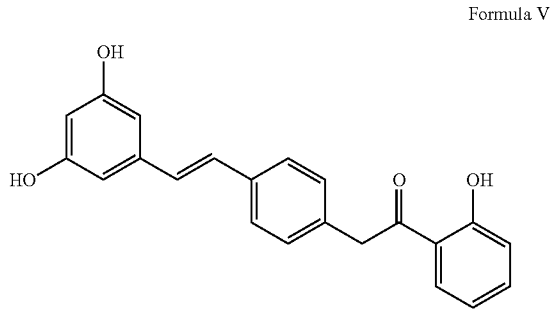 [SMILES: O=C(Cc1ccc(/C=C/c2cc(O)cc(O)c2)cc1)c1ccccc1O]

or a pharmaceutically acceptable salt or prodrug thereof.

In some embodiments, the method comprises, consists essentially of or consists of administering to said subject a therapeutically effective amount of a compound of Formula VI Formula VI

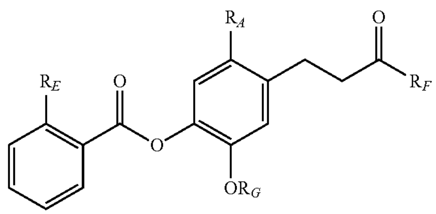

or a pharmaceutically acceptable salt or prodrug thereof, wherein $R_E$ is —H, —OH, or —O—$C_{1-6}$ acyl; $R_F$ is optionally substituted $C_{1-12}$ alkyl or optionally substituted $C_{1-12}$ alkenyl; and $R_G$ is —H or $C_{1-6}$ alkyl. In some such embodiments, $R_E$ is —O—C(O)—$C_{1-3}$ alkyl. In some such embodiments, $R_E$ is —OH, —O—C(O)-Me, —O—C(O)-Et, —O—C(O)—Pr, or —O—C(O)-Bu. In some such embodiments, $R_G$ is —H or -Me. In some such embodiments, $R_E$ is —O—C(O)-Me and $R_G$ is -Me. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is

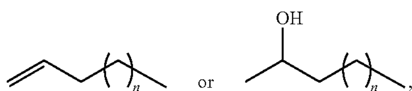

wherein n=3, 5, or 7. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments $R_G$ is -Me; $R_E$ is —OH or —O—C(O)-Me; and $R_F$ is optionally substituted $C_{2-7}$ alkyl or optionally substituted $C_{2-7}$ alkenyl. In some such embodiments, $R_G$ is —H or -Me; $R_E$ is —OH, —O—C(O)-Me, —O—C(O)-Et, —O—C(O)—Pr, or —O—C(O)-Bu; and $R_F$ is:

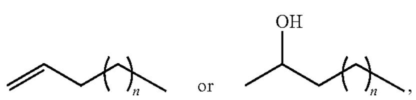

wherein n=3, 5, or 7; in some variations, n=3; in some variations n=5; in some variations n=7.

In some embodiments, the method comprises, consists essentially of or consists of administering to said subject a therapeutically effective amount of a compound of Formula VII Formula VII

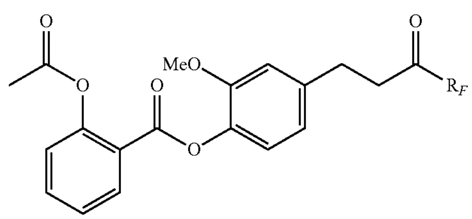

or a pharmaceutically acceptable salt or prodrug thereof, wherein $R_F$ is optionally substituted $C_{1-12}$ alkyl or optionally substituted $C_{1-12}$ alkenyl. In some such embodiments, $R_F$ is optionally substituted $C_{1-9}$ alkyl or optionally substituted $C_{1-9}$ alkenyl. In some such embodiments, $R_F$ is optionally substituted $C_{1-7}$ alkyl or optionally substituted $C_{1-7}$ alkenyl. In some such embodiments, $R_F$ is optionally substituted $C_{2-7}$ alkyl or optionally substituted $C_{2-7}$ alkenyl. In some such embodiments, $R_F$ is optionally substituted $C_{2-9}$ alkyl or optionally substituted $C_{2-9}$ alkenyl. In some such embodiments, $R_F$ is optionally substituted $C_{2-11}$ alkyl or optionally substituted $C_{2-11}$ alkenyl. In some embodiments, $R_F$ is optionally substituted $C_7$ alkyl or optionally substituted $C_7$ alkenyl. In some such embodiments, $R_F$ is optionally substituted $C_9$ alkyl or optionally substituted $C_9$ alkenyl. In some such embodiments, $R_F$ is optionally substituted $C_{11}$ alkyl or optionally substituted $C_{11}$ alkenyl. In some such embodiments, $R_F$ is

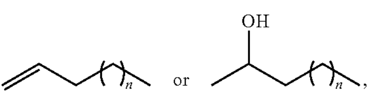

wherein n=3, 5, or 7; in some variations, n=3; in some variations n=5; in some variations n=7.

In some embodiments, the method comprises, consists essentially of or consists of administering to said subject a therapeutically effective amount of a pharmaceutical composition of the present invention.

In some embodiments, the method comprises, consists essentially of or consists of administering to said subject a therapeutically effective amount of a compound comprising a first moiety and a second moiety, wherein the first and second moieties are covalently linked, wherein the first moiety is aspirin, an aspirin analog or an aspirin derivative and wherein the second moiety is stilbene, an analog or derivative of stilbene, gingerol, an analog or derivative of gingerol, shogaol, an analog or derivative of shogaol, zingerone or an analog or derivative of zingerone.

In some such embodiments, the composition is a compound of the present invention. In some such embodiments, the composition is a pharmaceutical composition of the present invention. In some such embodiments, the composition is a compound comprising a first moiety and a second moiety, wherein the first and second moieties are covalently linked, wherein the first moiety is aspirin, an aspirin analog or an aspirin derivative and wherein the second moiety is stilbene, an analog or derivative of stilbene, gingerol, an analog or derivative of gingerol, shogaol, an analog or derivative of shogaol, zingerone or an analog or derivative of zingerone.

In some embodiments, administration of the composition results in the prevention and/or treatment of a first disorder and the prevention and/or treatment of a second disorder. For example, administration of the composition may result in the treatment of rectal cancer and the prevention of colon cancer (by preventing metastasis, for example).

In some embodiments, the subject exhibits one or more risk factors associated with the disorder. For example, the subject may have a familial history of cancer, one or more pre-cancerous lesions, premalignant cells, preneoplastic cells or other aberrant phenotypes indicating probably progression to a cancerous state.

In some embodiments, the subject is a human.

In some embodiments, the composition is administered in combination with surgery, radiation therapy, chemotherapy, gene therapy, RNA therapy, adjuvant therapy, immunotherapy, nanotherapy or a combination thereof.

In some embodiments, the method further comprises administering to the subject at least one supplemental agent. In some embodiments, the at least one supplemental agent comprises a therapeutic agent such as an antitumor alkylating agent, an antitumor antimetabolite, an antitumor antibiotics, a plant-derived antitumor agent, an antitumor organoplatinum compound, an antitumor campthotecin derivative, an antitumor tyrosine kinase inhibitor, a monoclonal antibody, an interferon, a biological response modifier, a hormonal antitumor agent, an angiogenesis inhibitor, an anti-metastatic agent, a differentiating agent, a chemotherapeutic agent, a chemopreventative agent, a gene therapy agent, an enzymatic inhibitor or a pharmaceutically acceptable salt or prodrug of any of the foregoing. In some such embodiments, the other therapeutic agent is administered prior to, concomitant with or subsequent to administering the composition of the present invention. In some such embodiments, the composition(s) of the present invention and the supplemental agent can act additively or, more preferably, synergistically.

Combination therapy may include the administration of a composition of the present invention and at least one supplemental agent as part of a specific treatment regimen intended to provide the beneficial effect from the co-action of the therapeutic agents. The beneficial effects of the combination may include, but are not limited to, pharmacokinetic and/or pharmacodynamic co-action resulting from the combination of therapeutic agents. Administration of the therapeutic agents in combination may be carried out over a defined time period (e.g., minutes, hours, days or weeks, depending upon the combination selected). Combination therapy can be carried out either sequentially or substantially simultaneously. In the case of sequential administration of more than one therapeutic agent, each therapeutic agent is administered at a different time. In the case of simultaneous administration, at least two of the therapeutic agents are administered in a substantially simultaneous manner, either in the same pharmaceutical composition or in different pharmaceutical compositions. Substantially simultaneous administration can be accomplished, for example, by administering to the subject a single capsule having a fixed ratio of each therapeutic agent or in multiple, single capsules for each of the therapeutic agents. In one embodiment, a composition comprising a conjugate of the application is administered concurrently with the administration of another therapeutic agent, which can be part of the same composition as the conjugate of the application or a different composition. In another embodiment, a composition comprising a conjugate of the application is administered prior to, or subsequent to, administration of another therapeutic agent.

Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected can be administered by intravenous injection while the other therapeutic agents of the combination can be administered orally. Alternatively, for example, all therapeutic agents can be administered orally or all therapeutic agents can be administered by intravenous injection. The sequence in which the therapeutic agents are administered is not narrowly critical. In some embodiments, the therapeutic agents are administered within about 1 minute, 5 minutes, 10 minutes, 15 minutes, 20 minutes, 25 minutes, 30 minutes, 40 minutes, 50 minutes, 1 hour, 1.5 hours, 2 hours, 2.5 hours, 3 hours, 3.5 hours, 4 hours, 4.5 hours, 5 hours, 5.5 hours, 6 hours, 7 hours, 8 hours, 9 hours, 10 hours, 11 hours, 12 hours, 1 day, 2 days, 3 days, 4 days, 5 days, 6 days, 1 week, 2 weeks, 3 weeks or 4 weeks of one another.

Combination therapy also encompasses the administration of the conjugate as described above in further combination with other therapies including but not limited to chemotherapy, surgery, radiation therapy, gene therapy, immunotherapy, RNA therapy, adjuvant therapy, nanotherapy or a combination thereof. Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, by a significant period of time. The conjugate and the other pharmacologically active agent can be administered to a subject simultaneously, sequentially or in combination. It will be appreciated that when using a combination of the application, the conjugate of the application and the other pharmacologically active agent can be in the same pharmaceutically acceptable carrier and therefore administered simultaneously. They can be in separate pharmaceutical carriers such as conventional oral dosage forms which are taken simultaneously. The term "combination" further refers to the case where the compounds are provided in separate dosage forms and are administered sequentially.

The composition may be administered using any suitable method known in the art, including, but not limited to, oral, parenteral (e.g., intraarterial, intravenous (i.v.), subcutaneous, intramuscular and intrathecal), intraperitoneal (i.p.), intrarectal, intravaginal, intranasal, intragastric, intratracheal, sublingual, transcutaneous, intrapulmonary and topical administration. In some embodiments, the compound or pharmaceutical composition is administered orally, parenterally, topically or rectally. In some embodiments, the compound or pharmaceutical composition is administered via inhalation (e.g., as a spray or powder). In some embodiments, the compound or pharmaceutical composition is injected directly into a tumor. In some embodiments, the compound or pharmaceutical composition is administered as a depot formulation. In some embodiments, the compound or pharmaceutical composition is administered intraarterially and/or intravenously via a catheter.

Methods of the present invention may be used to prevent, diagnose, monitory and/or treat any suitable disorder, including, but not limited to, cancer. In some embodiments, the disorder is a gastrointestinal cancer, such as an anal cancer, an esophageal cancer, a stomach cancer, a liver cancer, a gallbladder cancer, a pancreatic cancer, a colon cancer or a rectal cancer. In some embodiments, the disorder is lung cancer. In some embodiments, the disorder is a metastatic disorder (e.g., metastatic cancer).

In some embodiments, administration of the composition produces fewer and/or less pronounced adverse effects (e.g., adverse GI effects associated with the administration of aspirin) than the individual moieties that make up the compound. For example, administration of a conjugate compound comprising an aspirin derivative and a stilbene derivative may produce fewer adverse effects than administration of the aspirin derivative and the stilbene derivative (and/or administration of aspirin and stilbene themselves). Administration of a sustained-release formulation of the composition may further reduce any adverse effects, allowing for the administration of higher dosages of the composition.

In some embodiments, administration of the composition produces greater and/or more prolonged therapeutic effects than the individual moieties that make up the compound. For example, administration of a conjugate compound comprising aspirin and gingerol may have a more pronounced antitumorigenesis effect than administration of aspirin and gingerol (and/or administration of an aspirin derivative/analog and a gingerol derivative/analog). Accordingly, methods of the present invention may achieve adequate levels of antitumor efficacy at a lower dosage than would be required for administration of the individual moieties that make up the compound.

It will be understood that the specific dosage level for any particular subject will depend on a variety of factors including, but not limited to, the activity of the composition being administered; the age, body weight, general health, sex and diet of the subject; the time and route of administration; the rate of excretion; and other drugs which have previously been administered.

Convenient dosing includes, but is not limited to, a once a day or twice a day administration, such as a tablet or capsule, as well as intravenous infusions. The use of time-release preparations to control the rate of release of the compound of the present invention as well as continuous infusions may also be employed. The dose may be administered in as many divided doses as is convenient.

Unit dosage formulations can be those containing a daily dose or unit, daily sub-dose, or an appropriate fraction thereof, of a composition of the present invention. The unit dose may be for oral consumption, such as by a tablet or capsule, or for infusion, or administered by other means as disclosed herein. In some embodiments, the dose amount is provided once a day, twice a day, 3 times a day, or 4 or more times a day. In other embodiments, the dose amount is provided twice a week, once a week, twice a month or once a month. For example, a dose can be provided twice a day, 3 times a day, or 4 or more times a day. In some embodiments, such a dose is provided twice a week, once a week, twice a month or once a month. The amount may be provided by oral consumption, infusion, or administered by other means familiar to those of skill in the art, such as transdermal or transmucosal.

In some embodiments, the unit dose may be provided as an infusion. For example, the compositions described herein can be administered intravenously, such as by an IV drip using IV solutions well known in the art (e.g., isotonic saline (0.9% NaCl) or dextrose solution (e.g., 5% dextrose), optionally the intravenous solution further includes preservatives, e.g. Sodium metabisulfite. For example, a dose can be provided by infusion, such as by IV drip once a day, twice a week, once a week, twice a month or once a month. Alternately, the unit dose is infused once a day, twice a day, 3 times a day, or 4 or more times a day, for a period of time.

In some embodiments, the unit dose is from about 0.5 to about 500 mg/kg, about 0.5 to about 450 mg/kg, about 0.5 to about 400 mg/kg, about 0.5 to about 350 mg/kg, about 0.5 to about 300 mg/kg, about 0.5 to about 250 mg/kg, about 0.5 to about 200 mg/kg, about 0.5 to about 150 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 0.5 to about 5 mg/kg; about 1 to about 500 mg/kg, about 1 to about 450 mg/kg, about 1 to about 400 mg/kg, about 1 to about 350 mg/kg, about 1 to about 300 mg/kg, about 1 to about 250 mg/kg, about 1 to about 200 mg/kg, about 1 to about 150 mg/kg, about 1 to about 100 mg/kg, about 1 to about 50 mg/kg, about 1 to about 25 mg/kg, about 1 to about 20 mg/kg, about 1 to about 15 mg/kg, about 1 to about 10 mg/kg, about 1 to about 5 mg/kg, about 2 to about 500 mg/kg, about 2 to about 450 mg/kg, about 2 to about 400 mg/kg, about 2 to about 350 mg/kg, about 2 to about 300 mg/kg, about 2 to about 250 mg/kg, about 2 to about 200 mg/kg, about 2 to about 150 mg/kg, about 2 to about 100 mg/kg, about 2 to about 50 mg/kg, about 2 to about 25 mg/kg, about 2 to about 20 mg/kg, about 2 to about 15 mg/kg, about 2 to about 10 mg/kg, about 2 to about 5 mg/kg, 3 to about 500 mg/kg; about 3 to about 450 mg/kg, about 3 to about 400 mg/kg, about 3 to about 350 mg/kg, about 3 to about 300 mg/kg, about 3 to about 250 mg/kg, about 3 to about 200 mg/kg, about 3 to about 150 mg/kg, about 3 to about 100 mg/kg, about 3 to about 50 mg/kg, about 3 to about 25 mg/kg, about 3 to about 20 mg/kg, about 3 to about 15 mg/kg, about 3 to about 10 mg/kg, or about 3 to about 5 mg/kg of a composition of the present invention (e.g., a compound of the present invention).

In some embodiments, the unit dose is at least about 2 μg/kg, 5 μg/kg, 10 μg/kg, 15 μg/kg, 20 μg/kg, 30 μg/kg, 40 μg/kg, 50 μg/kg, 60 μg/kg, 70 μg/kg, 80 μg/kg, 90 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 250 mg/kg, 300 mg/kg, 350 mg/kg. 400 mg/kg, 450 mg/kg, 500 mg/kg or more of a composition of the present invention (e.g., a compound of the present invention).

In some embodiments, the present invention provides a kit comprising, consisting essentially of or consisting of a compound or pharmaceutical composition of the present invention and instructions for using the compound or pharmaceutical composition to prevent, monitor and/or treat a disorder.

In some embodiments, the present invention provides a kit comprising, consisting essentially of or consisting of a composition of the present invention, a supplemental composition and instructions for using the composition of the present invention and the supplemental composition to prevent, monitor and/or treat a disorder.

Kits of the present invention may comprise instructions for preventing, monitoring and/or treating any suitable disorder, including, but not limited to, cancer. In some embodiments, the disorder is a gastrointestinal cancer, such as an anal cancer, an esophageal cancer, a stomach cancer, a liver cancer, a gallbladder cancer, a pancreatic cancer, a colon cancer or a rectal cancer. In some embodiments, the disorder is lung cancer.

Kits of the present invention may comprise instructions for preventing, monitoring and/or treating a disorder in any suitable subject, including, but not limited to, human subjects.

Kits of the present invention may comprise instructions for preventing, monitoring and/or treating a disorder according to a method of the present invention.

Kits of the present invention may comprise any suitable supplemental compound or composition, including, but not limited to, therapeutic compounds/compositions. In some embodiments, the supplemental compound or composition comprises an antitumor alkylating agent, an antitumor antimetabolite, an antitumor antibiotics, a plant-derived antitumor agent, an antitumor organoplatinum compound, an antitumor campthotecin derivative, an antitumor tyrosine kinase inhibitor, a monoclonal antibody, an interferon, a biological response modifier, a hormonal anti-tumor agent, an angiogenesis inhibitor, a differentiating agent or a pharmaceutically acceptable salt or prodrug of any of the foregoing. In some embodiments, the supplemental compound or composition comprises an active agent that reduces one or more adverse effects associated with administration of the compound or pharmaceutical composition of the present invention. In some embodiments, the supplemental compound or composition comprises an active agent that enhances the efficacy of the compound or pharmaceutical composition of the present invention.

EXAMPLES

The following examples are for illustrative purposes only and are not intended to be a detailed catalogue of all the different ways in which the present invention may be implemented or of all the features that may be added to the present invention.

Starting materials useful for preparing compounds of the present invention and intermediates thereof are commercially available and/or can be prepared by well-known synthetic methods. Other methods for synthesis of the compounds described herein are either described in the art or will be readily apparent to the skilled artisan in view of the references provided above and can be used to synthesize conjugates of the application. One skilled in the art will therefore appreciate that the following Examples are exemplary and that numerous changes, modifications, and alterations can be employed without departing from the scope of the presently disclosed subject matter.

Example 1

Synthesis of Aspirin-Stilbene Derivative Compounds

As shown in Scheme I below, stilbene derivatives can be reacted with acetylsalicyloyl chloride under basic conditions to yield conjugate compounds.

Scheme I

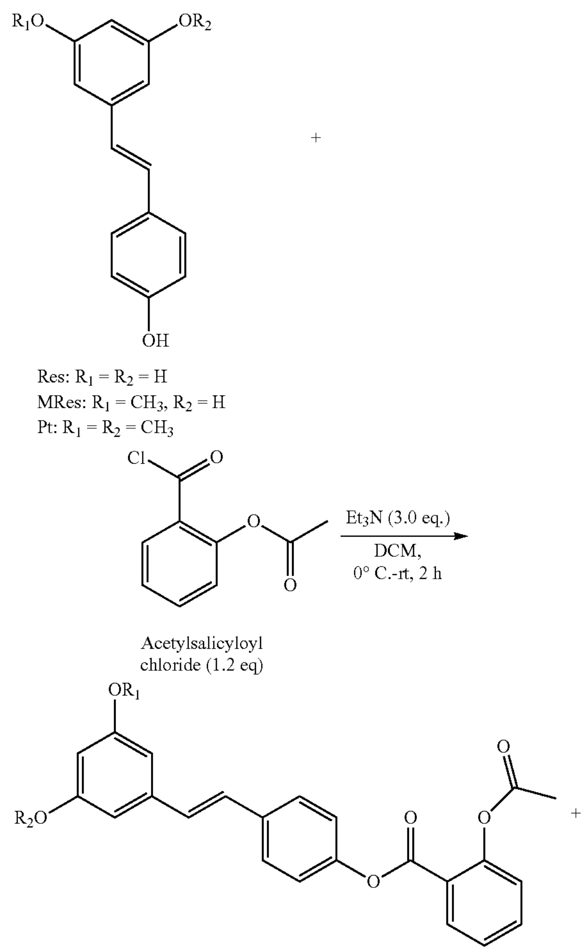

-continued

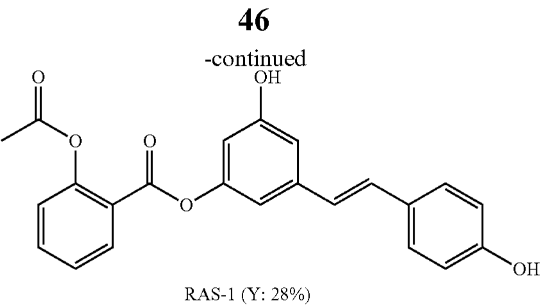

RAS-1 (Y: 28%)

Di-methylated resveratrol (pterostilbene; Pt) was reacted with 1.2 equivalents of acetylsalicyloyl chloride under basic conditions to generate pterostilbene aspirinate (PAS; yield: 96%). The structure of PAS was determined by $^{1}$H, $^{13}$C, and 2D (HMQC and HMBC) NMR and MS analysis.

PAS: white solid; $^{1}$H NMR (700 MHz, $CDCl_3$) δ 6.66 (2H, t, J=2.0 Hz, H-2/6), 6.39 (1H, t, J=2.0 Hz, H-4), 6.99 (1H, d, J=16.1 Hz, H-7), 7.07 (1H, d, J=16.1 Hz, H-8), 7.53 (2H, d, J=8.4 Hz, H-10/14), 7.16 (2H, d, J=8.4 Hz, H-11/13), 7.17 (1H, d, J=8.0 Hz, H-4'), 7.62 (1H, dt, J=8.0, 1.4 Hz, H-5'), 7.37 (1H, t, J=8.0 Hz, H-6'), 8.21 (1H, dd, J=8.0, 1.4 Hz, H-7'), 2.30 (3H, s, $C\underline{H}_3C{=}O$), and 3.81 (6H, s, OMe-3/5); $^{13}$C NMR (175 MHz, $CDCl_3$) δ 139.2 (s, C-1), 104.6 (d, C-2/6), 161.0 (s, C-3/5), 100.1 (d, C-4), 129.1 (d, C-7), 128.1 (d, C-8), 135.3 (s, C-9), 127.7 (d, C-10/14), 121.9 (d, C-11/13), 150.0 (s, C-12), 163.0 (s, C-1'), 122.5 (s, C-2'), 151.2 (s, C-3'), 124.1 (d, C-4'), 134.7 (d, C-5'), 126.3 (d, C-6'), 132.3 (d, C-7'), 169.8 (s, $CH_3\underline{C}C{=}O$), 21.1 (q, $\underline{C}H_3C{=}O$), and 55.4 (q, OMe-3/5); positive APCIMS, m/z 419 $[M+H]^+$.

Mono-methylated resveratrol (MRes) was reacted with 1.2 equivalents of acetylsalicyloyl chloride under basic conditions to generate mono-methylated resveratrol aspirinate (MRAS; yield: 80%). The structure of MRAS was determined by $^{1}$HNMR and MS analysis.

MRAS: white solid; $^{1}$H NMR (600 MHz, $CDCl_3$) δ 6.59 (1H, s, H-2), 6.34 (1H, t, J=2.1 Hz, H-4), 6.64 (1H, s, H-6), 7.06 (1H, d, J=16.3 Hz, H-7), 6.96 (1H, d, J=16.3 Hz, H-8), 7.53 (2H, d, J=8.6 Hz, H-10/14), 7.17 (2H, d, J=8.6 Hz, H-11/13), 7.19 (1H, d, J=8.0 Hz, H-4'), 7.65 (1H, dt, J=8.0, 1.6 Hz, H-5'), 7.40 (1H, t, J=8.0 Hz, H-6'), 8.23 (1H, dd, J=8.0, 1.6 Hz, H-7'), 2.32 (3H, s, $C\underline{H}_3C{=}O$), and 3.82 (3H, s, OMe-3); positive APCIMS, m/z 405 $[M+H]^+$.

Resveratrol (Res) was reacted with 1.2 equivalents of acetylsalicyloyl chloride under basic conditions to generate two resveratrol aspirinate isomers: RAS (yield: 65%) and RAS-1 (yield: 28%). The compound structures were determined by $^{1}$H NMR and MS analysis.

RAS: white solid; $^{1}$H NMR (600 MHz, $CD_3OD$) δ 6.89 (1H, s, H-2), 6.51 (1H, t, J=2.0 Hz, H-4), 6.84 (1H, s, H-6), 7.09 (1H, d, J=16.3 Hz, H-7), 6.93 (1H, d, J=16.3 Hz, H-8), 7.41 (2H, d, J=8.6 Hz, H-10/14), 6.79 (2H, d, J=8.6 Hz, H-11/13), 7.26 (1H, d, J=8.0 Hz, H-4'), 7.74 (1H, dt, J=8.0, 1.6 Hz, H-5'), 7.47 (1H, t, J=8.0 Hz, H-6'), 8.20 (1H, dd, J=8.0, 1.6 Hz, H-7'), and 2.30 (3H, s, $C\underline{H}_3C{=}O$); $^{13}$C NMR (125 MHz, $CD_3OD$); positive APCIMS, m/z 391 $[M+H]^+$.

RAS-1: white solid; $^{1}$H NMR (600 MHz, $CD_3OD$) δ 6.53 (2H, d, J=2.0 Hz, H-2/6), 6.24 (1H, t, J=2.0 Hz, H-4), 7.09 (1H, d, J=16.3 Hz, H-7), 7.03 (1H, d, J=16.3 Hz, H-8), 7.61 (2H, d, J=8.6 Hz, H-10/14), 7.18 (2H, d, J=8.6 Hz, H-11/13), 7.26 (1H, d, J=8.0 Hz, H-4'), 7.73 (1H, dt, J=8.0, 1.6 Hz, H-5'), 7.47 (1H, t, J=8.0 Hz, H-6'), 8.21 (1H, dd, J=8.0, 1.6 Hz, H-7'), and 2.29 (3H, s, $C\underline{H}_3C{=}O$); positive APCIMS, m/z 391 $[M+H]^+$.

Example 2

Synthesis of Aspirin-Shogaol Compounds

As shown in Scheme II below, shogaol and shogaol derivatives can be reacted with acetylsalicyloyl chloride under basic conditions to yield a conjugate compound.

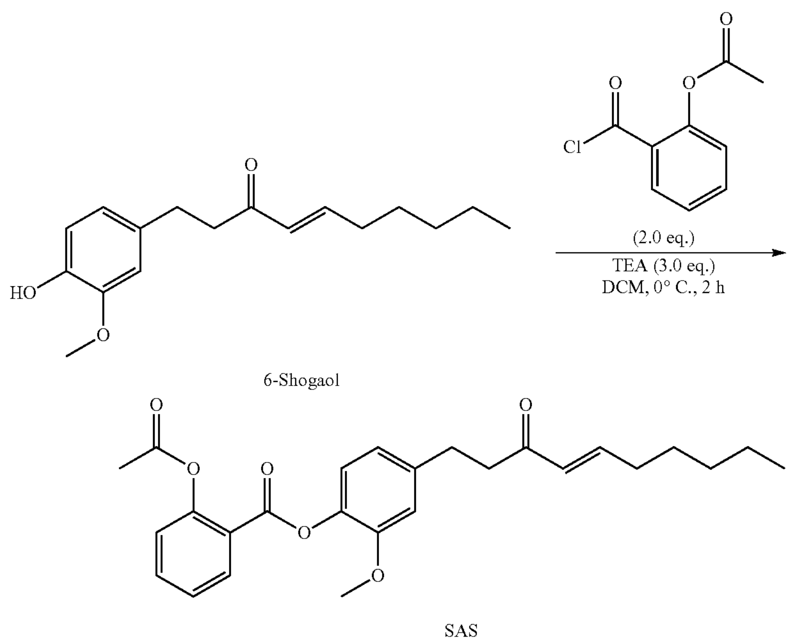

6-Shogaol was reacted with 2.0 equivalents of acetylsalicyloyl chloride under basic conditions to generate 6-shogaol aspirinate (SAS; yield: 93%). Its structure was determined by $^{1}$HNMR and MS analysis.

SAS: yellow oil; $^{1}$H NMR (600 MHz, $CDCl_3$) δ 6.85 (1H, d, J=1.7 Hz, H-2), 7.02 (1H, d, J=8.0 Hz, H-5), 6.80 (1H, dd, J=8.0, 1.7 Hz, H-6), 2.94 (2H, t, J=−7.2 Hz, H-1'), 2.88 (2H, t, J=7.2 Hz, H-2'), 6.11 (1H, d, J=17.0 Hz, H-4'), 6.84 (1H, dt, J=17.0, 7.0 Hz, H-5'), 2.21 (2H, m, H-6'), 1.47 (2H, m, H-7'), 1.35-1.25 (4H, m, H-8'/9'), 0.90 (3H, t, J=6.8 Hz, H-10'), 7.16 (1H, d, J=8.0 Hz, H-4'), 7.62 (1H, dt, J=8.0, 1.6 Hz, H-5'), 7.37 (1H, t, J=8.0 Hz, H-6'), 8.23 (1H, dd, J=8.0, 1.6 Hz, H-7'), 2.29 (3H, s, $C\underline{H}_3C{=}O$), and 3.80 (3H, s, OMe-3); positive APCIMS, m/z 439 $[M+H]^+$.

Aspirin-shogaol derivative compounds are formed by substituting 6-shogaol with 8-shogaol or 10-shogaol in Scheme II. The structures of the resulting conjugate compounds are determined by $^{1}$HNMR and MS analysis.

Example 3

Synthesis of Aspirin-Gingerol Compounds

As shown in Scheme III below, gingerol and gingerol derivatives can be reacted with acetylsalicyloyl chloride under basic conditions to yield a conjugate compound.

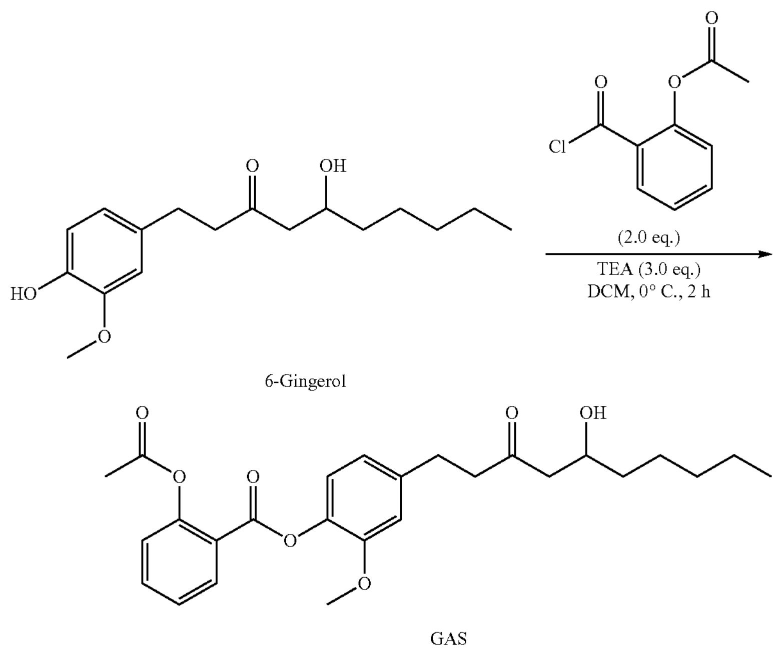

6-Gingerol was reacted with 2.0 equivalents acetylsalicyloyl chloride under basic conditions to generate 6-gingerol aspirinate (GAS; yield: 99%). Its structure was determined by $^{1}$HNMR and MS analysis.

GAS: yellow oil; $^{1}$H NMR (600 MHz, $CDCl_3$) δ 6.82 (1H, d, J=1.7 Hz, H-3), 6.78 (1H, dd, J=8.0, 1.7 Hz, H-5), 7.02 (1H, d, J=8.0 Hz, H-6), 2.91 (2H, t, J=7.2 Hz, H-1'), 2.78 (2H, t, J=7.2 Hz, H-2'), 2.59 (1H, dd, J=17.3, 2.8 Hz, H-4'a), 2.51 (1H, dd, J=17.3, 9.1 Hz, H-4'b), 4.04 (1H, m, H-5'), 1.50-1.47 (2H, m, H-6'), 1.43-1.39 (2H, m, H-7'), 1.35-1.25 (4H, m, H-8'/9'), 0.89 (3H, t, J=7.0 Hz, H-10'), 7.16 (1H, d, J=8.0 Hz, H-3"), 7.62 (1H, dt, J=8.0, 1.6 Hz, H-4"), 7.37 (1H, t, J=8.0 Hz, H-5"), 8.23 (1H, dd, J=8.0, 1.6 Hz, H-6"), 2.29 (3H, s, H-8"), and 3.80 (3H, s, OMe-2); positive APCIMS, m/z 457 $[M+H]^+$.

Aspirin-gingerol derivative compounds are formed by substituting 6-gingerol with 8-gingerol or 10-gingerol in Scheme III. The structures of the resulting conjugate compounds are determined by $^{1}$HNMR and MS analysis.

Example 4

Synthesis of (E)-(4-(3,5-dihydroxystyryl)phenyl)(2-hydroxyphenyl)methanone

Bromostilene is produced by a Wittig reaction of 3,5-dimethoxybenzaldehyde with (4-bromobenzyl)-triphenylphosphonium bromide. Bromine-lithium exchange of bromide with n-butyllithium, followed by treatment of salicylic aldehyde gives the benzylic alcohol. Oxidation by copper of the benzylic alcohol gives the ketone. Finally, demethylation of the ketone generates product (E)-(4-(3,5-dihydroxystyryl)phenyl)(2-hydroxyphenyl)methanone (Formula IV; 131). Its structure is determined by $^{1}$HNMR and MS analysis.

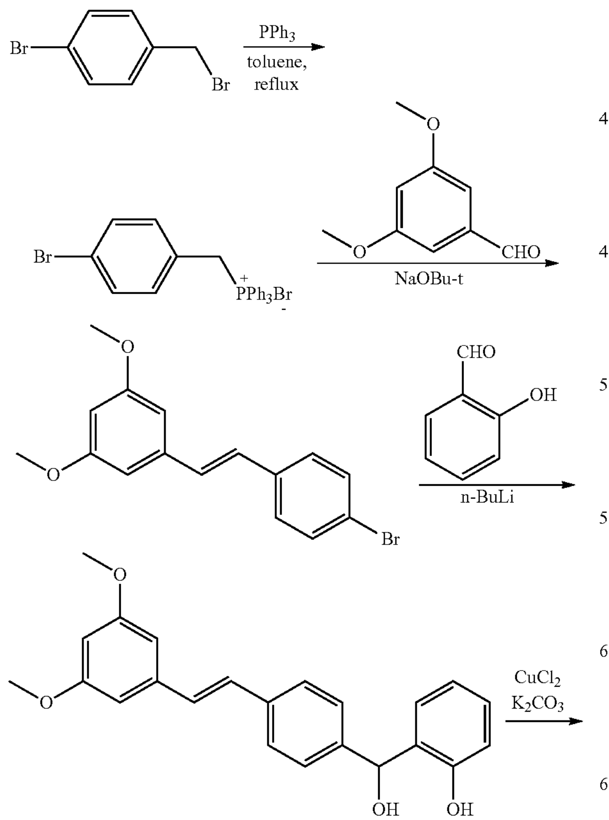

-continued

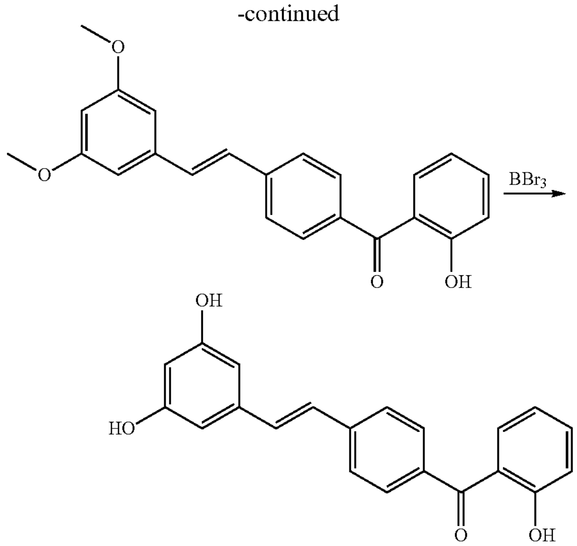

Example 5

Synthesis of (E)-2-(4-(3,5-dihydroxystyryl)phenyl)-1-(2-hydroxyphenyl)ethanone Reductive coupling of 1-bromo-4-(bromomethyl)benzene with O-acetylsalicyloyl chloride produces a ketone, which is treated by boron tribromide to form the deacetylated product. A Heck reaction of the deacetylated product with 1,3-dimethoxy-5-vinylbenzene yields the ortho-hydroxy ketone. Demethylation of the ortho-hydroxy ketone gives the desired product (E)-2-(4-(3,5-dihydroxystyryl)phenyl)-1-(2-hydroxyphenyl)ethanone (Formula V; 152). Its structure is determined by $^{1}$H NMR and MS analysis.

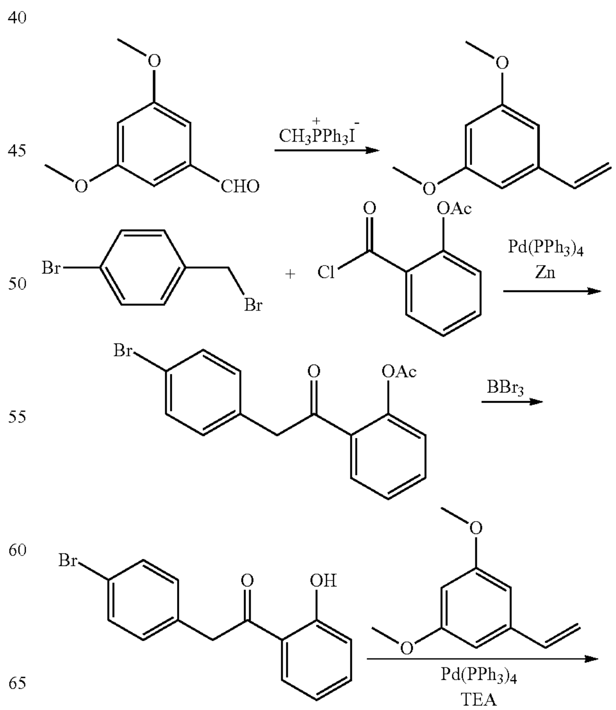

-continued

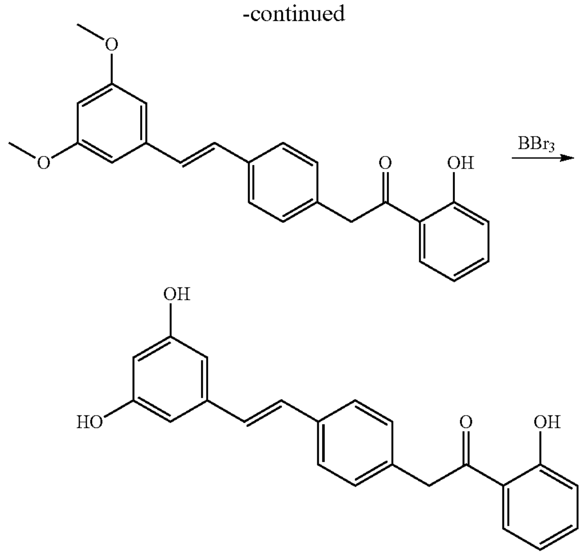

Example 6

Effect of Aspirin-Stilbene Derivative Compounds on Colon Cancer Cell Lines

The effects of the aspirin-stilbene derivative conjugates compared to standards were evaluated based on the inhibition of growth of HCT-116 and HT-29 human colon cancer cells. Cells were plated in 96-well plates in growth medium with 10% FBS. After 24 h, the medium was replaced with fresh medium containing test agent with desired final concentration (20, 30, 40, 50, and 60 μM), and the cells were incubated for 48 h. Viable cells were analyzed using the MTT assay, and the results are shown (FIG. 1) relative to control. Each value represents the mean±S.D. (n=8). FIG. 1A summarizes the results for aspirin (As), Res, RAS, RAS-1, and the combination of resveratrol and aspirin (Res+As). RAS had a stronger growth inhibitory effect than resveratrol and aspirin alone, and stronger than the combination of resveratrol and aspirin (1:1) on both HCT-116 and HT-29 human colon cancer cells (FIG. 1A). FIG. 1B summarizes the results for As, MRes, MRAS and the combination of MRes and aspirin (MRes+As). MRAS had weaker growth inhibitory effects than MRes and the combination of MRes and aspirin (1:1). FIG. 1C summarizes the results for As, Pt, PAS, and the combination of pterostilbene and aspirin (Pt+As). PAS had weaker growth inhibitory effects than pterostilbene and the combination of pterostilbene and aspirin (1:1). In addition, RAS had much stronger growth inhibitory effects than RAS-1, MRAS, and PAS.

Example 7

Effect of Aspirin-Shogaol Compounds on Colon Cancer Cell Lines

The effects of As, 6-shogaol (6-s), SAS and the combination of 6-shogaol and aspirin (6-s+As) on the growth of HCT-116 and HT-29 human colon cancer cells and H1299 human lung cancer cells were measured. Cells were plated in 96-well plates in growth medium with 10% FBS. After 24 h, the medium was replaced with fresh medium containing test agent with desired final concentration (5, 7.5, 10, 15, and 20 μM), and the cells were incubated for 48 h. Viable cells were analyzed using the MTT assay, and the results are shown relative to control (FIG. 2).

Figure 2:
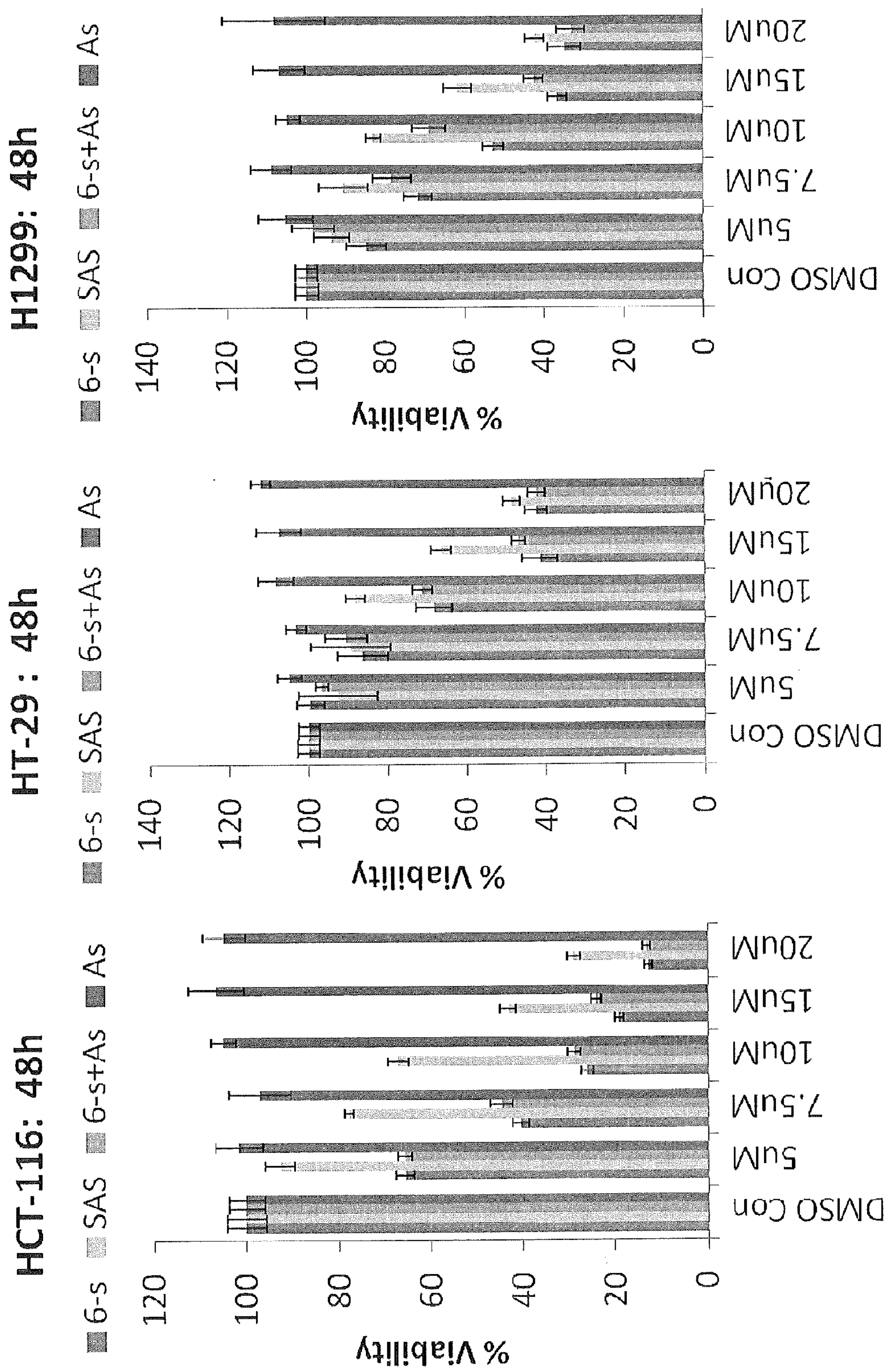
FIG. 2 shows the effects of 6-shogaol (6-s), 6-shogaol aspirinate (SAS), combination of 6-shogaol and aspirin (6-s+As), and aspirin (As) on the growth of HCT-116 and HT-29 human colon cancer cells and H1299 human lung cancer cells.

SAS had a stronger growth inhibitory effect than aspirin alone, but less effective than 6-shogaol alone and the combination of 6-shogaol and aspirin (1:1) on all cell lines (HCT-116, HT-29, and H-1299) (FIG. 2; each value represents the mean±standard deviation (n=8)).

Example 8

Effect of Aspirin-Gingerol Compounds on Colon Cancer Cell Lines

The effects of As, 6-gingerol (6g), GAS, and the combination of 6-gingerol and aspirin (6g+As) on the growth of HCT-116 and HT-29 human colon cancer cells and H1299 human lung cancer cells were measured. Cells were plated in 96-well plates in growth medium with 10% FBS. After 24 h, the medium was replaced with fresh medium containing test agent with desired final concentration (20, 40, 60, 80, and 100 μM), and the cells were incubated for 48 h. Viable cells were analyzed using the MTT assay, and the results are shown relative to control (FIG. 3).

Figure 3:
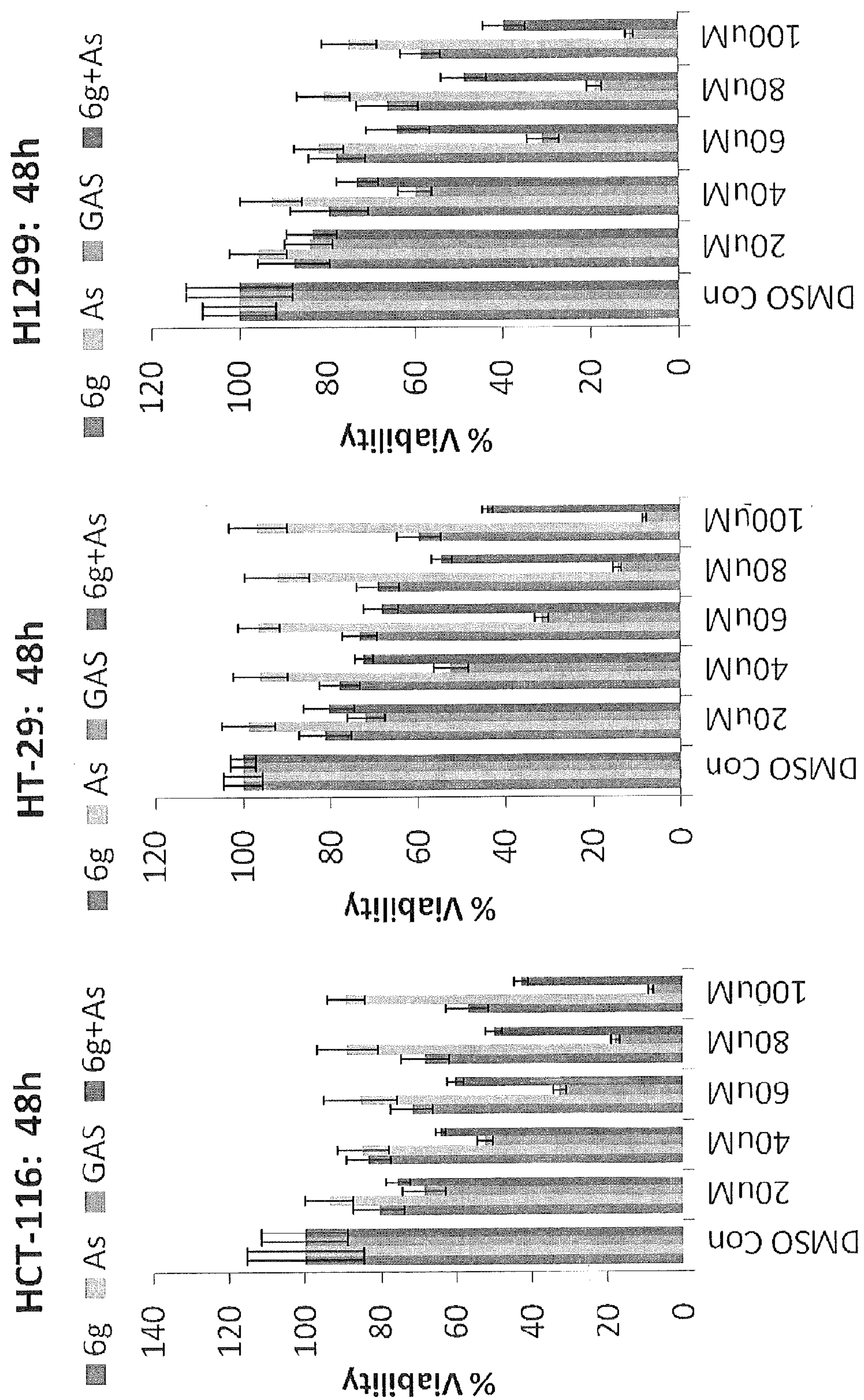
FIG. 3 shows the effects of 6-gingerol (6g), aspirin (As), 6-gingerol aspirinate (GAS), and combination of 6-gingerol and aspirin (6g+As) on the growth of HCT-116 and HT-29 human colon cancer cells and H1299 human lung cancer cells.

GAS had a much stronger growth inhibitory effect than 6-gingerol and aspirin alone, as well as the combination of 6-gingerol and aspirin (1:1) on all cell lines (HCT-116, HT-29, and H-1299) (FIG. 3; each value represents the mean±standard deviation (n=8).

Example 9

Effect of Aspirin-Resveratrol Compounds on Colon Cancer Cell Lines

Figure 4:
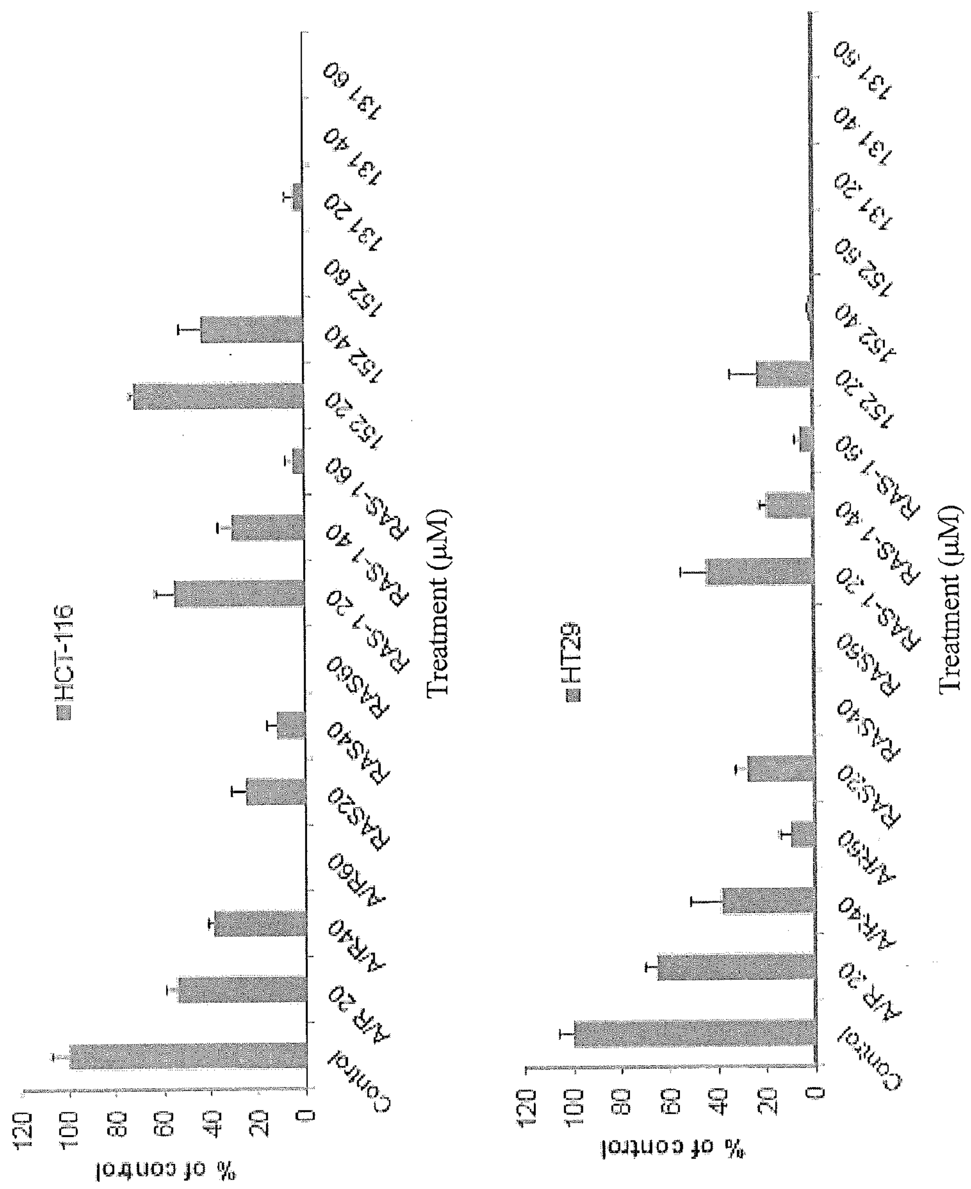
FIG. 4 shows the effects of aspirin and resveratrol (A/R), RAS, RAS-1, 152 and 131 on the growth of HCT-116 and HT-29 human colon cancer cells at various concentrations.

The effects of the combination of aspirin and resveratrol (A/R), RAS, RAS-1, 131 and 152 on colony formation of HCT-116 and HT-29 colon cancer cells were measured. HCT-116 (100 cells/well) and HT-29 (100 cells/well) cells were seeded in six-well plates. After 24 h, cells were treated with various concentrations (20, 40, and 60 M) of the test compound. After 14 days of culture, media were removed and colonies were washed with PBS. Colonies were then stained with 0.5% crystal violet for 30 min. After thorough rinsing with PBS, the colonies were counted and recorded. FIG. 4 shows the anti-cell proliferation effect of the test agents using a colony formation assay.

Example 10

Urinary Metabolic Profile of PAS and RAS in Mice

The metabolic profile of Pt using LC/MS 23 was investigated. PAS was administered to mice (n=5) by oral gavage (200 mg/kg), and urine samples were collected in metabolism cages for 24 h after administration of vehicle (control mice) or PAS. LC/MS methods were developed to analyze PAS, pterostilbene, and aspirin. LC chromatograms of urine samples collected from PAS-treated mice obtained using positive APCI-MS interface (FIG. 5): (A) before and (B) after enzymatic hydrolysis (treated with P-glucuronidase and sulfatase); using negative ESI-MS interface: (C) before and (D) after enzymatic hydrolysis.

Figure 5:
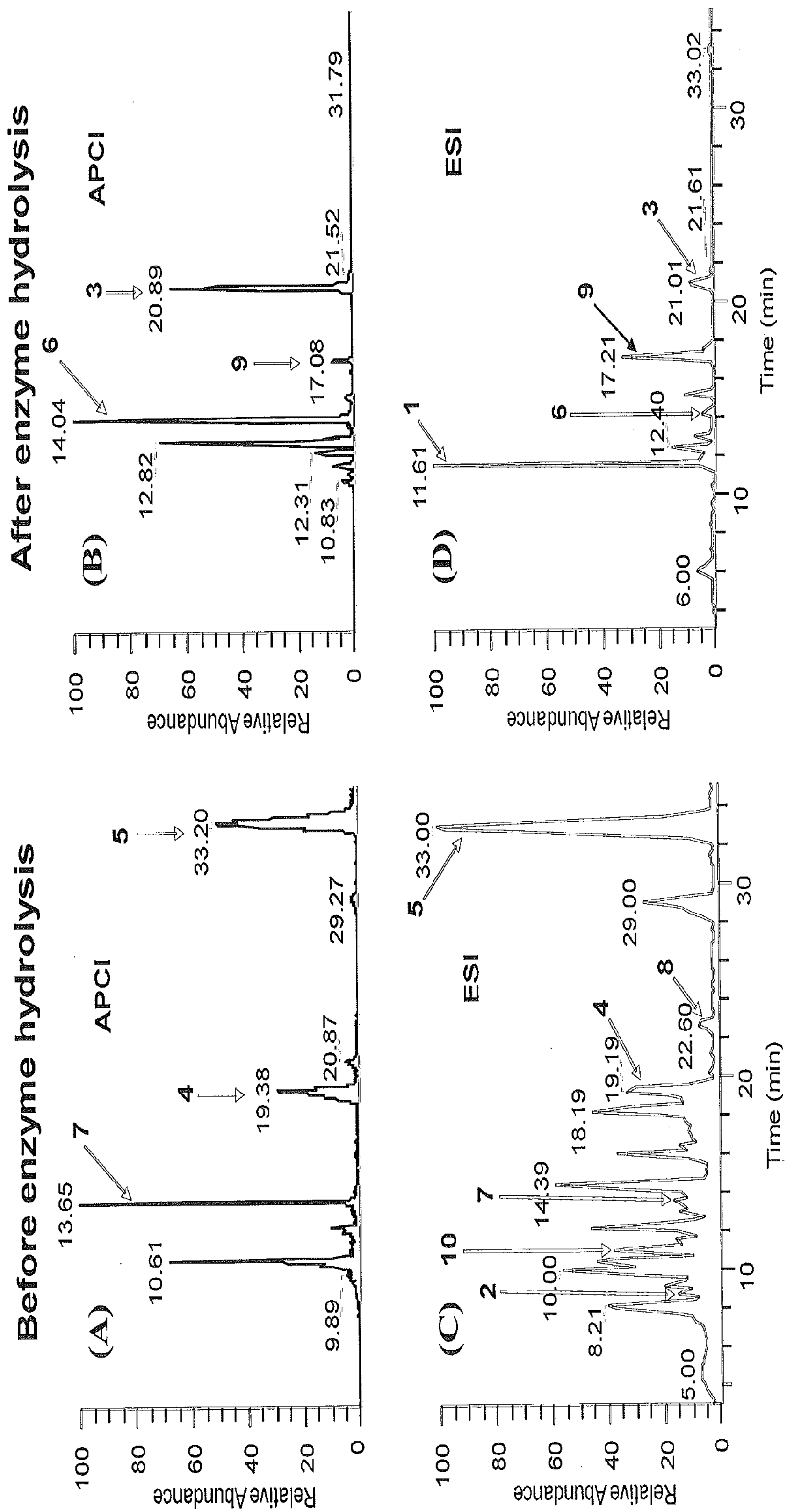
FIG. 5 shows liquid chromatography (LC) chromatograms of urine samples collected from PAS-treated mice obtained using positive APCI-MS interface: (A) before and (B) after enzymatic hydrolysis (treated with β-glucuronidase and sulfatase); using negative ESI-MS interface: (C) before and (D) after enzymatic hydrolysis.

As shown in FIG. 5, Peak 1: salicylic acid; peak 2: salicylic acid glucuronide; peak 3: pterostilbene; peak 4: pterostilbene glucuronide; peak 5: pterostilbene sulfate; peak 6: mono-demethylated pterostilbene; peak 7: mono-demethylated pterostilbene glucuronide; peak 8: mono-demethylated pterostilbene sulfate; peak 9: mono-hydroxylated pterostilbene; and peak 10: mono-hydroxylated pterostilbene glucuronide.

PAS had the highest response under positive APCI/MS mode, and aspirin and salicylic acid had the highest response under negative ESIMS mode. Both positive APCI/MS and negative ESI/MS modes are sensitive to pterostilbene. However, aspirin and salicylic acid are hardly detectable under positive APCI/MS mode, and PAS is not detectable under negative ESI/MS mode. Therefore, APCI/MS positive mode was used to analyze PAS, pterostilbene, and their metabolites, and ESI/MS negative mode was used to analyze aspirin, pterostilbene, and their metabolites. PAS was hydrolyzed in mice to generate metabolites of aspirin and pterostilbene; neither PAS nor its deacetylated metabolites were detected.

Using the same experimental conditions, RAS has also been shown to be hydrolyzed in human colon cancer cells (HCT-116 and HT-29) to generate resveratrol and aspirin. Generally aspirin-stilbene derivative conjugates can be hydrolyzed and are effective prodrugs of both aspirin and the stilbene derivatives.

Example 11

Xenograft Study 8 week old animals are randomized into 4 groups based on treatment (DMSO: n=7; RAS 50 mg/kg: n=7; RAS 100 mg/kg: n=7; R+As (resveratrol+aspirin in 1:1 molar ratio equivalent to 50 mg/kg RAS): n=7). Animals are implanted with $2\times10^6$ HCT-116 cells on each flank. Starting one week post implantation, animals receive their respective treatments through oral gavage (1001 in corn oil and 5% DMSO), 7×/week for up to 3 weeks. Tumor volume is measured every other day during treatment regimen. At no more than 3 weeks of treatment, animal are sacrificed. The tumors are weighed and evaluated for biomarker analysis, bioavailability and histological analysis.

Although the present invention has been described with reference to specific details of certain embodiments thereof, it is not intended that such details should be regarded as limitations upon the scope of the invention except as and to the extent that they are included in the accompanying claims. As noted above, the above-described embodiments can be modified or varied without departing from the present invention. It is therefore to be understood that, within the scope of the claims and their equivalents, the present invention can be practiced otherwise than as specifically described above.

All patents, patent publications, non-patent publications referenced herein are incorporated by reference in their entireties for all purposes and to the same extent as if each was specifically and individually indicated to be incorporated by reference.

That which is claimed is:

1. A compound having the following structure

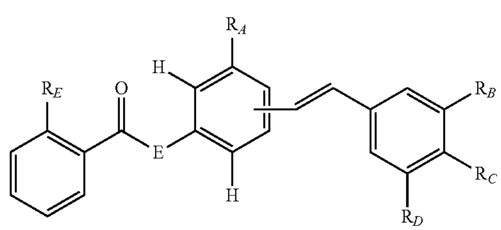

or a pharmaceutically acceptable salt or prodrug thereof, wherein:

E is —O—;

each of $R_A$ and $R_C$ is independently —H or —OH;

each of $R_D$ and $R_B$ is independently —H, —OH or —O—$C_{1-6}$ alkyl; and $R_E$ is —O—$C_{1-6}$ acyl.

2. The compound of claim 1, wherein $R_A$ is —OH.

3. The compound of claim 1, wherein said compound has the structure

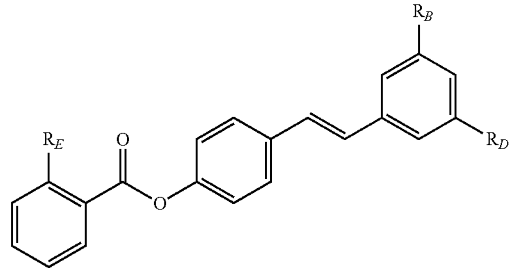

wherein:

each of $R_B$ and $R_D$ is independently —OH or —O—$C_{1-6}$ alkyl; and $R_E$ is —O—C(O)-Me.

4. The compound of claim 3, wherein each of $R_B$ and $R_D$ is —OH.

5. The compound of claim 3, wherein each of $R_B$ and $R_D$ is independently —O—$C_{1-6}$ alkyl.

6. The compound of claim 3, wherein each of $R_B$ and $R_D$ is independently —O—$C_{1-3}$ alkyl.

7. The compound of claim 3, wherein each of $R_B$ and $R_D$ is —O-Me.

8. The compound of claim 1, wherein said compound has the structure

Formula III

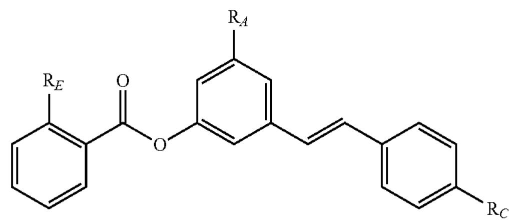

wherein:

$R_A$ is —OH;

$R_C$ is —H or —OH; and $R_E$ is —O—$C_{1-6}$ acyl.

9. The compound of claim 8, wherein $R_C$ is —OH and $R_E$ is —O—C(O)Me.

10. A compound of Formula IV or Formula V

Formula IV

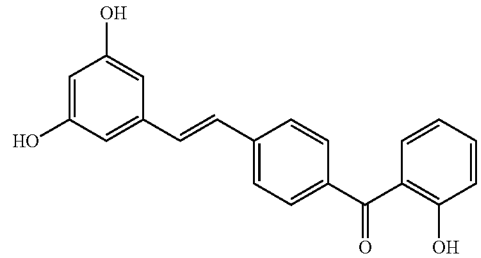

Formula V

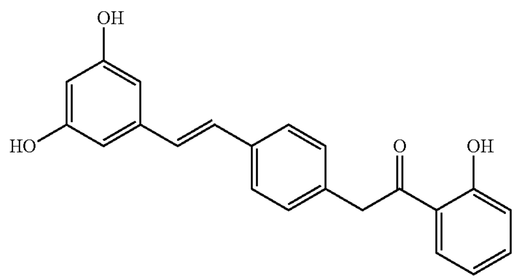

or a pharmaceutically acceptable salt or prodrug thereof.

11. A pharmaceutical composition, comprising:

a compound having the following structure

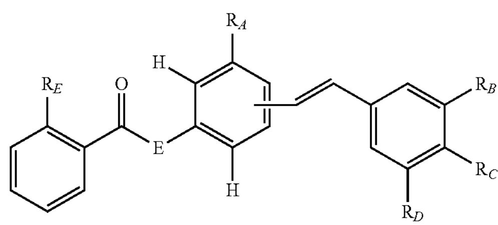

or pharmaceutically acceptable salt thereof; and a pharmaceutically acceptable carrier, wherein:

E is —O—;

each of $R_A$ and $R_C$ is independently —H or —OH;

each of $R_D$ and $R_B$ is independently —H, —OH or —O—$C_{1-6}$ alkyl; and $R_E$ is —O—$C_{1-6}$ acyl.

12. The pharmaceutical composition of claim 11, wherein said compound has the following structure

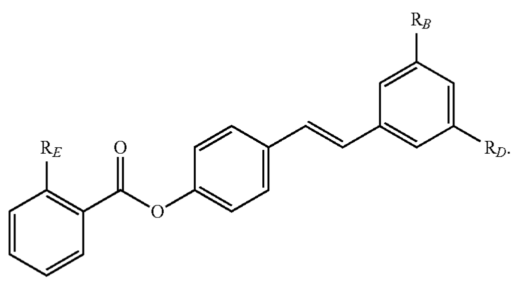

wherein:

each of $R_B$ and $R_D$ is independently —OH or —O—$C_{1-6}$ alkyl; and $R_E$ is —O—C(O)-Me.

13. The pharmaceutical composition of claim 12, wherein each of $R_B$ and $R_D$ is —OH.

14. The pharmaceutical composition of claim 12, wherein each of $R_B$ and $R_D$ is —O-Me.

15. The pharmaceutical composition of claim 11, wherein said compound has the following structure

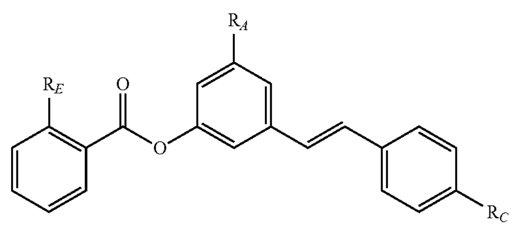

wherein:

$R_A$ is —OH;

$R_C$ is —H or —OH; and $R_E$ is —O—$C_{1-6}$ acyl.

16. The pharmaceutical composition of claim 15, wherein $R_C$ is —OH and $R_E$ is —O—C(O)Me.

17. A pharmaceutical composition, comprising:

a compound of Formula IV or Formula V

Formula IV

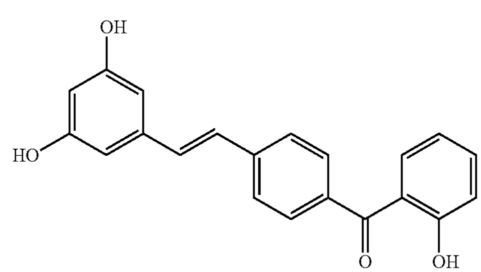

Formula V

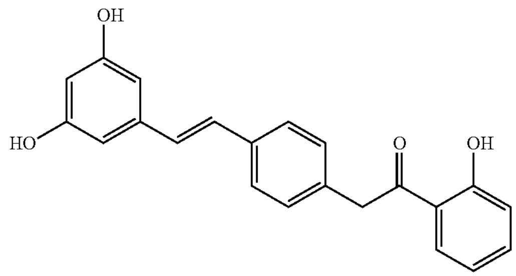

or a pharmaceutically acceptable salt or prodrug thereof; and a pharmaceutically acceptable carrier.

18. A compound having the following structure:

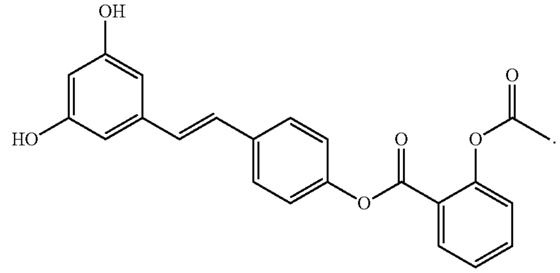 [SMILES: CC(=O)Oc1ccccc1C(=O)Oc1ccc(/C=C/c2cc(O)cc(O)c2)cc1]

* * * * *